(12) United States Patent
Angara et al.

(10) Patent No.: US 11,704,688 B2
(45) Date of Patent: *Jul. 18, 2023

(54) SPINAL CORD STIMULATOR SYSTEM

(71) Applicant: Cirtec Medical Corporation, Brooklyn Park, MN (US)

(72) Inventors: Raghavendra Angara, Norristown, PA (US); Saif Khalil, Wayne, PA (US); Miles Curtis, Philadelphia, PA (US); Christopher Biele, King of Prussia, PA (US); Daniel Fellmeth, Eagleville, PA (US)

(73) Assignee: Cirtec Medical Corp., Brooklyn Park, MN (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/072,885

(22) Filed: Oct. 16, 2020

(65) Prior Publication Data

US 2021/0035154 A1    Feb. 4, 2021

Related U.S. Application Data

(63) Continuation of application No. 15/839,951, filed on Dec. 13, 2017, now Pat. No. 10,810,614, which is a
(Continued)

(51) Int. Cl.
*A61N 1/378* (2006.01)
*A61N 1/36* (2006.01)
(Continued)

(52) U.S. Cl.
CPC ..... *G06Q 30/0244* (2013.01); *A61N 1/36071* (2013.01); *A61N 1/3787* (2013.01);
(Continued)

(58) Field of Classification Search
CPC .. A61N 1/3787; A61N 1/36071; A61N 1/025; A61N 1/0553; A61N 1/36125;
(Continued)

(56) References Cited

U.S. PATENT DOCUMENTS 3,195,540 A    7/1965 Waller
3,718,134 A    2/1973 Brindley
(Continued)

FOREIGN PATENT DOCUMENTS

CA    2491018 A1    12/2004
JP    2005531371 A    10/2005

*Primary Examiner* — Joseph M Dietrich
*Assistant Examiner* — Michael T. Holtzclaw
(74) *Attorney, Agent, or Firm* — Haynes and Boone, LLP

(57) ABSTRACT

A wireless charger system for inductively charging a rechargeable battery of an implantable pulse generator (IPG) implanted in a human body is provided. A charging coil in the charger is wirelessly coupled to a receiving coil of the IPG to charge the rechargeable battery. An end-of-charge (EOC) circuit continuously monitors the reflected impedance from a reflected impedance sensor and determines the end of charge when a predetermined pattern of the reflected impedance corresponding to an EOC signal from the IPG is received.

Advantageously, receiving the EOC signal through the charging coil eliminates the need to provide a separate communication circuit in the IPG that communicates with the charger.

20 Claims, 15 Drawing Sheets

Related U.S. Application Data continuation of application No. 14/642,810, filed on Mar. 10, 2015, now Pat. No. 9,872,997, which is a continuation-in-part of application No. 14/173,510, filed on Feb. 5, 2014, now Pat. No. 9,440,076.

(60) Provisional application No. 61/792,654, filed on Mar. 15, 2013.

(51) Int. Cl.

| | | |
|---|---|---|
| *A61N 1/02* | (2006.01) | |
| *A61N 1/05* | (2006.01) | |
| *A61N 1/372* | (2006.01) | |
| *G06Q 30/0242* | (2023.01) | |
| *H02J 50/90* | (2016.01) | |
| *H02J 50/70* | (2016.01) | |
| *H02J 50/12* | (2016.01) | |
| *G06Q 30/0251* | (2023.01) | |
| *G06Q 30/0241* | (2023.01) | |
| *A61N 1/375* | (2006.01) | |

(52) U.S. Cl.
CPC ..... *G06Q 30/0254* (2013.01); *G06Q 30/0277* (2013.01); *H02J 50/12* (2016.02); *H02J 50/70* (2016.02); *H02J 50/90* (2016.02); *A61N 1/025* (2013.01); *A61N 1/0553* (2013.01); *A61N 1/36125* (2013.01); *A61N 1/36142* (2013.01); *A61N 1/3752* (2013.01); *A61N 1/37229* (2013.01); *A61N 1/37235* (2013.01)

(58) Field of Classification Search
CPC ............ A61N 1/36142; A61N 1/37229; A61N 1/37235; A61N 1/3752; G06Q 30/0244; G06Q 30/0254; G06Q 30/0277; H02J 50/12; H02J 50/70; H02J 50/90
USPC .......................................................... 607/46
See application file for complete search history.

(56) References Cited

U.S. PATENT DOCUMENTS

| | | |
|---|---|---|
| 3,724,467 A | 4/1973 | Avery et al. |
| 3,727,616 A | 4/1973 | Lenzkes |
| 3,822,708 A | 7/1974 | Zilber |
| 3,867,950 A | 2/1975 | Fischell |
| 3,888,260 A | 6/1975 | Fischell |
| 3,942,535 A | 3/1976 | Schulman |
| 4,014,346 A | 3/1977 | Brownlee et al. |
| 4,019,518 A | 4/1977 | Maurer et al. |
| 4,082,097 A | 4/1978 | Mann et al. |
| 4,134,408 A | 1/1979 | Brownlee et al. |
| 4,234,679 A | 11/1980 | Schulman |
| 4,379,462 A | 4/1983 | Borkan et al. |
| 4,390,023 A | 6/1983 | Rise |
| 4,408,608 A | 10/1983 | Daly et al. |
| 4,459,989 A | 7/1984 | Borkan |
| 4,510,936 A | 4/1985 | Fourcin et al. |
| 4,512,351 A | 4/1985 | Pohndorf |
| 4,541,432 A | 9/1985 | Molina-Negro et al. |
| 4,549,556 A | 10/1985 | Tarjan et al. |
| 4,608,986 A | 9/1986 | Beranek et al. |
| 4,640,286 A | 2/1987 | Thomson |
| 4,690,145 A | 9/1987 | King-Smith et al. |
| 4,712,558 A | 12/1987 | Kidd et al. |
| 5,036,850 A | 8/1991 | Owens |
| 5,119,832 A | 6/1992 | Xavier |
| 5,143,067 A | 9/1992 | Rise et al. |
| 5,255,691 A | 10/1993 | Otten |
| 5,279,292 A | 1/1994 | Baumann et al. |
| 5,314,457 A | 5/1994 | Jeutter et al. |
| 5,354,320 A | 10/1994 | Schaldach et al. |
| 5,374,285 A | 12/1994 | Valani et al. |
| 5,391,193 A | 2/1995 | Thompson |
| 5,411,537 A | 5/1995 | Munshi et al. |
| 5,417,719 A | 5/1995 | Hull et al. |
| 5,441,527 A | 8/1995 | Erickson et al. |
| 5,443,486 A | 8/1995 | Hrdlicka et al. |
| 5,458,629 A | 10/1995 | Baudino et al. |
| 5,458,631 A | 10/1995 | Xavier |
| 5,501,703 A | 3/1996 | Holsheimer et al. |
| 5,591,217 A | 1/1997 | Barreras |
| 5,630,835 A | 5/1997 | Brownlee |
| 5,643,330 A | 7/1997 | Holsheimer et al. |
| 5,662,689 A | 9/1997 | Elsberry et al. |
| 5,690,693 A | 11/1997 | Wang et al. |
| 5,702,431 A | 12/1997 | Wang et al. |
| 5,713,939 A | 2/1998 | Nedungadi et al. |
| 5,733,313 A | 3/1998 | Barreras et al. |
| 5,733,322 A | 3/1998 | Starkebaum |
| 5,769,877 A | 6/1998 | Barreras, Sr. |
| 5,843,146 A | 12/1998 | Cross, Jr. |
| 5,861,019 A | 1/1999 | Sun et al. |
| 5,865,843 A | 2/1999 | Baudino |
| 5,893,883 A | 4/1999 | Torgerson et al. |
| 5,895,416 A | 4/1999 | Barreras et al. |
| 5,913,882 A | 6/1999 | King |
| 5,935,159 A | 8/1999 | Cross, Jr. et al. |
| 5,938,690 A | 8/1999 | Law et al. |
| 6,009,350 A | 12/1999 | Renken |
| 6,052,624 A | 4/2000 | Mann |
| 6,052,923 A | 4/2000 | Fenner et al. |
| 6,120,502 A | 9/2000 | Michelson |
| 6,167,312 A | 12/2000 | Goedeke |
| 6,169,925 B1 | 1/2001 | Villaseca et al. |
| 6,175,769 B1 | 1/2001 | Errico et al. |
| 6,181,969 B1 | 1/2001 | Gord |
| 6,181,971 B1 | 1/2001 | Doan |
| 6,185,452 B1 | 2/2001 | Schulman et al. |
| 6,185,463 B1 | 2/2001 | Baudino |
| 6,205,361 B1 | 3/2001 | Kuzma et al. |
| 6,208,894 B1 | 3/2001 | Schulman et al. |
| 6,216,045 B1 | 4/2001 | Black et al. |
| 6,227,204 B1 | 5/2001 | Baumann et al. |
| 6,236,892 B1 | 5/2001 | Feier |
| 6,240,317 B1 | 5/2001 | Villaseca et al. |
| 6,240,318 B1 | 5/2001 | Philips |
| 6,249,705 B1 | 6/2001 | Snell |
| 6,249,707 B1 | 6/2001 | Kohnen et al. |
| 6,266,564 B1 | 7/2001 | Hill et al. |
| 6,309,401 B1 | 10/2001 | Redko et al. |
| 6,379,300 B1 | 4/2002 | Haubrich |
| 6,381,496 B1 | 4/2002 | Meadows et al. |
| 6,393,325 B1 | 5/2002 | Mann et al. |
| 6,415,187 B1 | 7/2002 | Kuzma et al. |
| 6,456,256 B1 | 9/2002 | Amundson et al. |
| 6,456,887 B1 | 9/2002 | Dudding et al. |
| 6,463,329 B1 | 10/2002 | Goedeke |
| 6,473,653 B1 | 10/2002 | Schallhorn et al. |
| 6,477,424 B1 | 11/2002 | Thompson et al. |
| 6,505,072 B1 | 1/2003 | Linder et al. |
| 6,505,401 B1 | 1/2003 | Doan |
| 6,516,227 B1 | 2/2003 | Meadows et al. |
| 6,522,932 B1 | 2/2003 | Kuzma et al. |
| 6,535,766 B1 | 3/2003 | Thompson et al. |
| 6,539,253 B2 | 3/2003 | Thompson et al. |
| 6,553,263 B1 | 4/2003 | Meadows et al. |
| 6,553,264 B2 | 4/2003 | Redko et al. |
| 6,587,724 B2 | 7/2003 | Mann |
| 6,600,954 B2 | 7/2003 | Cohen et al. |
| 6,609,031 B1 | 8/2003 | Law et al. |
| 6,609,032 B1 | 8/2003 | Woods et al. |
| 6,614,406 B2 | 9/2003 | Amundson et al. |
| 6,622,048 B1 | 9/2003 | Mann et al. |
| 6,650,944 B2 | 11/2003 | Goedeke et al. |
| 6,654,642 B2 | 11/2003 | Boydston et al. |
| 6,658,297 B2 | 12/2003 | Loeb |
| 6,658,302 B1 | 12/2003 | Kuzma et al. |
| 6,662,052 B1 | 12/2003 | Sanwal et al. |
| 6,662,053 B2 | 12/2003 | Borkan |
| 6,664,763 B2 | 12/2003 | Echarri et al. |
| 6,671,544 B2 | 12/2003 | Baudino |

(56) References Cited

U.S. PATENT DOCUMENTS

| | | |
|---|---|---|
| 6,675,045 B2 | 1/2004 | Mass et al. |
| 6,675,046 B2 | 1/2004 | Holsheimer |
| 6,708,065 B2 | 3/2004 | Von Arx et al. |
| 6,741,892 B1 | 5/2004 | Meadows et al. |
| 6,745,079 B2 | 6/2004 | King |
| 6,757,970 B1 | 7/2004 | Kuzma et al. |
| 6,795,737 B2 | 9/2004 | Gielen et al. |
| 6,809,701 B2 | 10/2004 | Amundson et al. |
| 6,819,958 B2 | 11/2004 | Weiner et al. |
| 6,847,849 B2 | 1/2005 | Mamo et al. |
| 6,850,802 B2 | 2/2005 | Holsheimer |
| 6,868,288 B2 | 3/2005 | Thompson |
| 6,871,099 B1 | 3/2005 | Whitehurst et al. |
| 6,889,086 B2 | 5/2005 | Mass et al. |
| 6,892,097 B2 | 5/2005 | Holsheimer |
| 6,895,280 B2 | 5/2005 | Meadows et al. |
| 6,895,283 B2 | 5/2005 | Erickson et al. |
| 6,901,292 B2 | 5/2005 | Hrdlicka et al. |
| 6,909,917 B2 | 6/2005 | Woods et al. |
| 6,920,359 B2 | 7/2005 | Meadows et al. |
| 6,930,602 B2 | 8/2005 | Dublin et al. |
| 6,937,891 B2 | 8/2005 | Leinders et al. |
| 6,941,171 B2 | 9/2005 | Mann et al. |
| 6,950,706 B2 | 9/2005 | Rodriguez et al. |
| 6,950,709 B2 | 9/2005 | Baudino |
| 6,981,314 B2 | 1/2006 | Black et al. |
| 6,985,088 B2 | 1/2006 | Goetz et al. |
| 6,993,384 B2 | 1/2006 | Bradley |
| 7,009,313 B1 | 3/2006 | Parramon et al. |
| 7,016,733 B2 | 3/2006 | Dublin et al. |
| 7,023,359 B2 | 4/2006 | Goetz et al. |
| 7,024,246 B2 | 4/2006 | Acosta et al. |
| 7,035,690 B2 | 4/2006 | Goetz |
| 7,039,470 B1 | 5/2006 | Wessman |
| 7,047,076 B1 | 5/2006 | Li et al. |
| 7,047,081 B2 | 5/2006 | Kuzman |
| 7,047,082 B1 | 5/2006 | Schrom et al. |
| 7,047,627 B2 | 5/2006 | Black et al. |
| 7,051,419 B2 | 5/2006 | Schrom et al. |
| 7,076,304 B2 | 7/2006 | Thompson |
| 7,099,718 B1 | 8/2006 | Thacker et al. |
| 7,107,102 B2 | 9/2006 | Daignault et al. |
| 7,110,824 B2 | 9/2006 | Amundson et al. |
| 7,127,296 B2 | 10/2006 | Bradley |
| 7,127,297 B2 | 10/2006 | Law et al. |
| 7,127,298 B1 | 10/2006 | He et al. |
| 7,142,909 B2 | 11/2006 | Greenberg et al. |
| 7,146,223 B1 | 12/2006 | King |
| 7,162,306 B2 | 1/2007 | Caby et al. |
| 7,174,215 B2 | 2/2007 | Bradley |
| 7,177,690 B2 | 2/2007 | Woods et al. |
| 7,177,691 B2 | 2/2007 | Meadows et al. |
| 7,177,702 B2 | 2/2007 | Wallace et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,206,642 B2 | 4/2007 | Pardo et al. |
| 7,211,103 B2 | 5/2007 | Greenberg et al. |
| 7,212,133 B2 | 5/2007 | Goetz et al. |
| 7,215,991 B2 | 5/2007 | Besson et al. |
| 7,225,032 B2 | 5/2007 | Schmeling et al. |
| 7,239,918 B2 | 7/2007 | Strother et al. |
| 7,239,920 B1 | 7/2007 | Thacker et al. |
| 7,248,929 B2 | 7/2007 | Meadows et al. |
| 7,254,443 B2 | 8/2007 | Jelen et al. |
| 7,254,445 B2 | 8/2007 | Law et al. |
| 7,254,446 B1 | 8/2007 | Erickson et al. |
| 7,263,406 B2 | 8/2007 | Toy et al. |
| 7,295,876 B1 | 11/2007 | Erickson |
| 7,295,878 B1 | 11/2007 | Meadows et al. |
| 7,310,873 B2 | 12/2007 | Pardo et al. |
| 7,317,948 B1 | 1/2008 | King et al. |
| 7,324,852 B2 | 1/2008 | Barolat et al. |
| 7,337,003 B2 | 2/2008 | Malinowski |
| 7,359,751 B1 | 4/2008 | Erickson et al. |
| 7,359,755 B2 | 4/2008 | Jones et al. |
| 7,363,079 B1 | 4/2008 | Thacker et al. |
| 7,369,897 B2 | 5/2008 | Boveja et al. |
| 7,376,466 B2 | 5/2008 | He et al. |
| 7,389,146 B2 | 6/2008 | Hanson et al. |
| 7,389,147 B2 | 6/2008 | Wahlstrand et al. |
| 7,428,438 B2 | 9/2008 | Parramon et al. |
| 7,437,193 B2 | 10/2008 | Parramon et al. |
| 7,437,197 B2 | 10/2008 | Harris et al. |
| 7,444,181 B2 | 10/2008 | Shi et al. |
| 7,444,184 B2 | 10/2008 | Bovega et al. |
| 7,463,927 B1 | 12/2008 | Chaouat |
| 7,471,986 B2 | 12/2008 | Hatlestad |
| 7,483,752 B2 | 1/2009 | Von Arx et al. |
| 7,489,966 B2 | 2/2009 | Leinders et al. |
| 7,496,404 B2 | 2/2009 | Meadows et al. |
| 7,499,755 B2 | 3/2009 | Cross, Jr. |
| 7,515,968 B2 | 4/2009 | Metzler et al. |
| 7,519,432 B2 | 4/2009 | Bolea et al. |
| 7,526,341 B2 | 4/2009 | Goetz et al. |
| 7,539,538 B2 | 5/2009 | Parramon et al. |
| 7,546,164 B2 | 6/2009 | King |
| 7,548,788 B2 | 6/2009 | Chinn et al. |
| 7,551,963 B2 | 6/2009 | Rusin et al. |
| 7,555,346 B1 | 6/2009 | Woods et al. |
| 7,571,001 B2 | 8/2009 | Thacker et al. |
| 7,580,753 B2 | 8/2009 | Kim et al. |
| 7,603,179 B1 | 10/2009 | Grandhe |
| 7,613,518 B2 | 11/2009 | Qin et al. |
| 7,617,006 B2 | 11/2009 | Metzler et al. |
| 7,630,749 B2 | 12/2009 | Squeri |
| 7,647,121 B2 | 1/2010 | Wahlstrand et al. |
| 7,650,192 B2 | 1/2010 | Wahlstrand |
| 7,657,319 B2 | 2/2010 | Goetz et al. |
| 7,658,196 B2 | 2/2010 | Ferreri et al. |
| 7,672,734 B2 | 3/2010 | Anderson et al. |
| 7,684,869 B2 | 3/2010 | Bradley et al. |
| 7,684,873 B2 | 3/2010 | Gerber |
| 7,697,995 B2 | 4/2010 | Cross, Jr. et al. |
| 7,706,888 B2 | 4/2010 | Jolly |
| 7,715,912 B2 | 5/2010 | Rezai et al. |
| 7,715,924 B2 | 5/2010 | Rezai et al. |
| 7,725,196 B2 | 5/2010 | Machado et al. |
| 7,729,781 B2 | 6/2010 | Swoyer et al. |
| 7,734,340 B2 | 6/2010 | De Ridder |
| 7,734,342 B2 | 6/2010 | Glelen et al. |
| 7,738,963 B2 | 6/2010 | Hickman et al. |
| 7,738,966 B2 | 6/2010 | Skubitz et al. |
| 7,742,821 B1 | 6/2010 | Vamos et al. |
| 7,743,810 B2 | 6/2010 | Moffitt et al. |
| 7,747,330 B2 | 6/2010 | Nolan et al. |
| 7,761,167 B2 | 7/2010 | Bennett et al. |
| 7,761,170 B2 | 7/2010 | Kaplan et al. |
| 7,761,985 B2 | 7/2010 | Hegland et al. |
| 7,765,005 B2 | 7/2010 | Stevenson |
| 7,765,011 B2 | 7/2010 | Skubitz et al. |
| 7,769,462 B2 | 8/2010 | Meadows et al. |
| 7,787,960 B2 | 8/2010 | Lubenow et al. |
| 7,797,048 B2 | 9/2010 | Stevenson et al. |
| 7,797,054 B2 | 9/2010 | Skubitz et al. |
| 7,797,057 B2 | 9/2010 | Harris |
| 7,801,600 B1 | 9/2010 | Carbunaru et al. |
| 7,801,602 B2 | 9/2010 | McClure et al. |
| 7,801,615 B2 | 9/2010 | Meadows et al. |
| 7,801,621 B1 | 9/2010 | Thacker et al. |
| 7,803,021 B1 | 9/2010 | Brase |
| 7,805,189 B2 | 9/2010 | Stein et al. |
| 7,805,197 B2 | 9/2010 | Bradley |
| 7,813,796 B2 | 10/2010 | Greenberg et al. |
| 7,813,803 B2 | 10/2010 | Heruth et al. |
| 7,813,809 B2 | 10/2010 | Strother et al. |
| 7,818,068 B2 | 10/2010 | Meadows et al. |
| 7,831,306 B2 | 11/2010 | Finch et al. |
| 7,831,311 B2 | 11/2010 | Cross, Jr. et al. |
| 7,831,313 B2 | 11/2010 | Lauro |
| 7,835,795 B2 | 11/2010 | Alexander et al. |
| 7,844,343 B2 | 11/2010 | Wahlstrand et al. |
| 7,848,817 B2 | 12/2010 | Janzig et al. |
| 7,848,818 B2 | 12/2010 | Barolat et al. |

(56) References Cited

U.S. PATENT DOCUMENTS

| | | |
|---|---|---|
| 7,848,819 B2 | 12/2010 | Goetz et al. |
| 7,848,820 B2 | 12/2010 | Abrahamson |
| 7,853,330 B2 | 12/2010 | Bradley et al. |
| 7,856,277 B1 | 12/2010 | Thacker et al. |
| 7,860,568 B2 | 12/2010 | Deininger et al. |
| 7,860,570 B2 | 12/2010 | Whitehurst et al. |
| 7,872,884 B2 | 1/2011 | Parramon et al. |
| 7,881,796 B2 | 2/2011 | Scott et al. |
| 7,881,805 B2 | 2/2011 | Bradley et al. |
| 7,885,712 B2 | 2/2011 | Goetz et al. |
| 7,891,085 B1 | 2/2011 | Kuzma et al. |
| 7,899,542 B2 | 3/2011 | Cowan et al. |
| 7,904,148 B2 | 3/2011 | Greenberg et al. |
| 7,908,013 B2 | 3/2011 | Miesel et al. |
| 7,930,030 B2 | 4/2011 | Woods et al. |
| 7,930,037 B2 | 4/2011 | Heruth et al. |
| 7,930,039 B2 | 4/2011 | Olson |
| 7,933,656 B2 | 4/2011 | Sieracki et al. |
| 7,937,158 B2 | 5/2011 | Erickson et al. |
| 7,941,227 B2 | 5/2011 | Barker |
| 7,949,393 B2 | 5/2011 | Varrichio et al. |
| 7,957,797 B2 | 6/2011 | Bourget et al. |
| 7,957,809 B2 | 6/2011 | Bourget et al. |
| 7,957,814 B2 | 6/2011 | Goetz et al. |
| 7,970,003 B2 | 6/2011 | Holt |
| 7,974,703 B2 | 7/2011 | Goetz et al. |
| 7,974,705 B2 | 7/2011 | Zdeblick et al. |
| 7,979,126 B2 | 7/2011 | Payne et al. |
| 7,979,131 B2 | 7/2011 | Feier et al. |
| 7,979,133 B2 | 7/2011 | Feier et al. |
| 7,983,757 B2 | 7/2011 | Miyazawa et al. |
| 7,983,762 B2 | 7/2011 | Gliner et al. |
| 7,983,766 B1 | 7/2011 | Thacker et al. |
| 7,987,000 B2 | 7/2011 | Moffitt et al. |
| 7,991,482 B2 | 8/2011 | Bradley |
| 7,996,091 B2 | 8/2011 | Harris |
| 8,000,794 B2 | 8/2011 | Lozano |
| 8,000,800 B2 | 8/2011 | Takeda et al. |
| 8,005,547 B2 | 8/2011 | Forsberg et al. |
| RE42,682 E | 9/2011 | Barreras et al. |
| 8,019,427 B2 | 9/2011 | Moffitt |
| 8,019,438 B2 | 9/2011 | Johnson et al. |
| 8,019,439 B2 | 9/2011 | Kuzma et al. |
| 8,019,440 B2 | 9/2011 | Kokones et al. |
| 8,019,443 B2 | 9/2011 | Schleicher et al. |
| 8,032,224 B2 | 10/2011 | Miesel et al. |
| 8,036,737 B2 | 10/2011 | Goetz et al. |
| 8,036,747 B2 | 10/2011 | Thacker et al. |
| 8,036,757 B2 | 10/2011 | Lee et al. |
| 8,044,635 B2 | 10/2011 | Peterson |
| 8,046,073 B1 | 10/2011 | Pianca |
| 8,050,769 B2 | 11/2011 | Gharib et al. |
| 8,055,337 B2 | 11/2011 | Moffitt et al. |
| 8,065,013 B2 | 11/2011 | Bradley et al. |
| 8,073,542 B2 | 12/2011 | Doerr |
| 8,082,034 B2 | 12/2011 | Keacher |
| 8,082,039 B2 | 12/2011 | Kim et al. |
| 8,086,317 B2 | 12/2011 | Finch et al. |
| 8,086,318 B2 | 12/2011 | Strother et al. |
| 8,108,048 B2 | 1/2012 | Masoud |
| 8,108,049 B2 | 1/2012 | King |
| 8,108,051 B2 | 1/2012 | Cross, Jr. et al. |
| 8,108,052 B2 | 1/2012 | Boling |
| 8,116,880 B2 | 2/2012 | Cross, Jr. |
| 8,121,697 B2 | 2/2012 | Greenberg et al. |
| 8,121,701 B2 | 2/2012 | Woods et al. |
| 8,121,702 B2 | 2/2012 | King |
| 8,126,567 B2 | 2/2012 | Gerber et al. |
| 8,131,358 B2 | 3/2012 | Moffitt et al. |
| 8,135,477 B2 | 3/2012 | Fattouh et al. |
| 8,140,168 B2 | 3/2012 | Olson et al. |
| 8,150,530 B2 | 4/2012 | Wesselink |
| 8,150,533 B2 | 4/2012 | Wessman |
| 8,155,750 B2 | 4/2012 | Jaax et al. |
| 8,155,752 B2 | 4/2012 | Aghassian et al. |
| 8,165,678 B2 | 4/2012 | Forsberg et al. |
| 8,170,674 B2 | 5/2012 | Pyles et al. |
| 8,170,675 B2 | 5/2012 | Alataris et al. |
| 8,175,719 B2 | 5/2012 | Shi et al. |
| 8,175,720 B2 | 5/2012 | Skelton et al. |
| 8,180,445 B1 | 5/2012 | Moffitt |
| 8,180,451 B2 | 5/2012 | Hickman et al. |
| 8,180,462 B2 | 5/2012 | Inman et al. |
| 8,185,207 B2 | 5/2012 | Molnar et al. |
| 8,185,212 B2 | 5/2012 | Carbunaru et al. |
| 8,195,297 B2 | 6/2012 | Penner |
| 8,195,304 B2 | 6/2012 | Strother et al. |
| 8,204,595 B2 | 6/2012 | Pianca et al. |
| 8,209,014 B2 | 6/2012 | Doerr |
| 8,209,021 B2 | 6/2012 | Alataris et al. |
| 8,214,051 B2 | 7/2012 | Sieracki et al. |
| 8,214,057 B2 | 7/2012 | Barolat |
| 8,224,453 B2 | 7/2012 | De Ridder |
| 8,260,425 B2 | 9/2012 | Kokones et al. |
| 8,285,388 B2 | 10/2012 | Wahlstrand |
| 2003/0191504 A1 | 10/2003 | Meadows et al. |
| 2005/0107841 A1 | 5/2005 | Meadows et al. |
| 2009/0024187 A1 | 1/2009 | Erickson et al. |
| 2009/0030487 A1 | 1/2009 | Lang |
| 2009/0270935 A1 | 10/2009 | Zhao et al. |
| 2009/0326608 A1 | 12/2009 | Huynh et al. |
| 2011/0184486 A1 | 7/2011 | De Ridder |
| 2013/0096651 A1 | 4/2013 | Ozawa et al. |
| 2014/0277264 A1 | 9/2014 | Khalil et al. |
| 2014/0314170 A1 | 10/2014 | Plumb et al. |

SPINAL CORD STIMULATOR SYSTEM

CROSS REFERENCE TO RELATED APPLICATIONS

The present application is a continuation of U.S. patent application Ser. No. 15/839,951, filed on Dec. 13, 2017, which is a continuation of U.S. patent application Ser. No. 14/642,810, filed on Mar. 10, 2015, now U.S. Pat. No. 9,872,997, issued on Jan. 23, 2018, which is a continuation-in-part of U.S. patent application Ser. No. 14/173,510, filed on Feb. 5, 2014, now U.S. Pat. No. 9,440,076, issued on Sep. 13, 2016, which claims priority to U.S. Provisional Application Ser. No. 61/792,654, filed Mar. 15, 2013, and titled "SPINAL CORD STIMULATOR SYSTEM," all of which are herein incorporated by reference in their entirety.

TECHNICAL FIELD

This disclosure relates to stimulators using electrical pulses in a medical context, and more particularly, applying electrical pulse stimulators to the spinal cord to control pain.

BACKGROUND

A Spinal Cord Stimulator (SCS) is used to exert pulsed electrical signals to the spinal cord to control chronic pain. Spinal cord stimulation, in its simplest form, comprises stimulating electrodes implanted in the epidural space, an implanted pulse generator (IPG) implanted in the lower abdominal area or gluteal region, conducting wires connecting the electrodes to the electrical pulse generator, an electrical pulse generator remote control, and an electrical pulse generator charger. Spinal cord stimulation has notable analgesic properties and, at the present, is used mostly in the treatment of failed back surgery syndrome, complex regional pain syndrome and refractory pain due to ischemia.

Electrotherapy of pain by neurostimulation began shortly after Melzack and Wall proposed the gate control theory in 1965. This theory proposed that nerves carrying painful peripheral stimuli and nerves carrying touch and vibratory sensation both terminate in the dorsal horn (the gate) of the spinal cord. It was hypothesized that input to the dorsal horn of the spinal cord could be manipulated to "close the gate" to the nerves. As an application of the gate control theory, Shealy et al. implanted the first spinal cord stimulator device directly on the dorsal column for the treatment of chronic pain in 1971.

Spinal cord stimulation does not eliminate pain. The electrical impulses from the stimulator override the pain messages so that the patient does not feel the pain intensely. In essence, the stimulator masks the pain. A trial implantation is performed before implanting the permanent stimulator. The physician first implants a trial stimulator through the skin (percutaneously) to perform stimulations as a trial run. Because a percutaneous trial stimulator tends to move from its original location, it is considered temporary. If the trial is successful, the physician can then implant a permanent stimulator. The permanent stimulator is implanted under the skin of the abdomen with the leads inserted under the skin and subcutaneously fed to and inserted into the spinal canal. This placement of the stimulator in the abdomen is a more stable, effective location. The leads, which consist of an array of electrodes, can be percutaneous type or paddle type. Percutaneous electrodes are easier to insert in comparison with paddle type, which are inserted via incision over spinal cord and laminectomy.

From time to time, the battery in the IPG needs to be charged wirelessly since the IPG is implanted in the patient's body. There are a number of problems that exist in currently available wireless chargers for the IPG. Problems include inefficient charging, improper charger alignment, difficulty of aligning the charger by patients and lack of ability for the charger to terminate charging when it is completed. Therefore, it would be desirable to provide a system and method for an improved charger for the SCS system.

SUMMARY

According to one aspect of the present invention, a wireless charger system for inductively charging a rechargeable battery of an implantable pulse generator (IPG) implanted in a human body is provided. A charging coil in the charger is wirelessly coupled to a receiving coil of the IPG to charge the rechargeable battery. An end-of-charge (EOC) circuit continuously monitors the reflected impedance from a reflected impedance sensor and determines the end of charge when a predetermined pattern of the reflected impedance corresponding to an EOC signal from the IPG is received. Advantageously, receiving the EOC signal through the charging coil eliminates the need to provide a separate communication circuit in the IPG that communicates with the charger.

According to another aspect of the present invention, a method for a wireless charger system for inductively charging a rechargeable battery of an IPG is provided. The method applies a charging signal that inductively charges the rechargeable battery of the IPG. A reflected impedance from a reflected impedance sensor is continuously monitored while the charging signal is being applied. The method determines an end-of-charge (EOC) when a predetermined pattern of the reflected impedance corresponding to an EOC signal from the IPG is received.

DETAILED DESCRIPTION

Implantable Pulse Generator (IPG)

Figure 1:
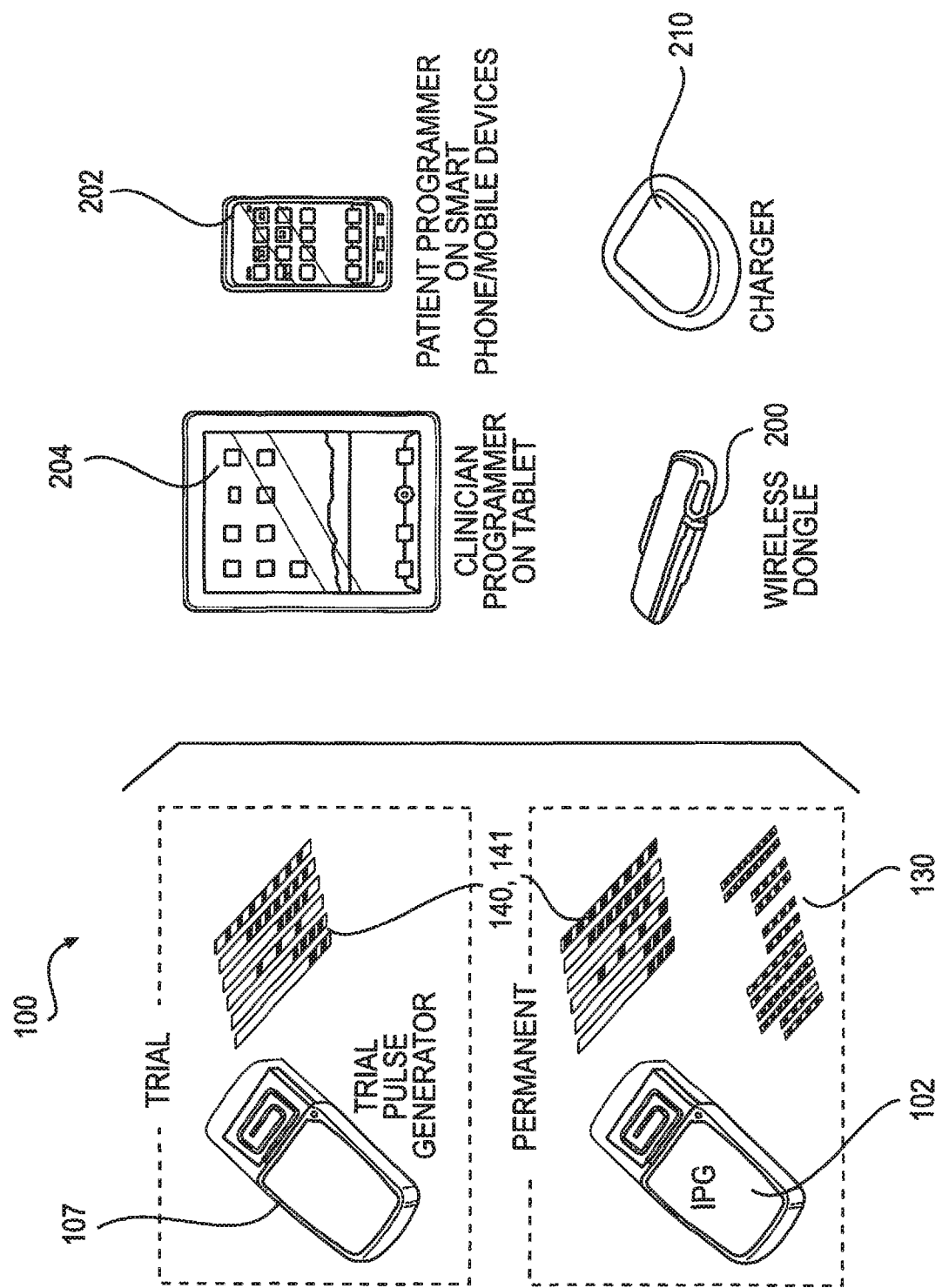
FIG. 1 depicts various components that can be included in a spinal cord stimulation system, according to an embodiment, during trial and permanent implantation.

FIG. 1 illustrates various components that can be included in a SCS system for the trial and the permanent installation periods. The spinal cord stimulator (SCS) 100 is an implantable device used to deliver electrical pulse therapy to the spinal cord in order to treat chronic pain. The implantable components of the system consist of an Implantable Pulse Generator (IPG) 102 and a multitude of stimulation electrodes 130. The IPG 102 is implanted subcutaneously, no more than 30 mm deep in an area that is comfortable for the patient while the stimulation electrodes 130 are implanted directly in the epidural space. The electrodes 130 are wired to the IPG 102 via leads 140, 141 which keep the stimulation pulses isolated from each other in order to deliver the correct therapy to each individual electrode 130.

The therapy delivered consists of electrical pulses with controlled current amplitude ranging from +12.7 to −12.7 mA (current range 0-25.4 mA). These pulses can be programmed in both length and frequency from 10 μS to 2000 μS and 0.5 Hz to 1200 Hz. At any given moment, the sum of the currents sourced from the anodic electrodes 130 must equal the sum of the currents sunk by the cathodic electrodes 130. In addition, each individual pulse is bi-phasic, meaning that once the initial pulse finishes another pulse of opposite amplitude is generated after a set holdoff period. The electrodes 130 may be grouped into stimulation sets in order to deliver the pulses over a wider area or to target specific areas, but the sum of the currents being sourced at any one given time may not exceed 20 mA. A user can also program different stimulation sets (up to eight) with different parameters in order to target different areas with different therapies.

Figure 2:
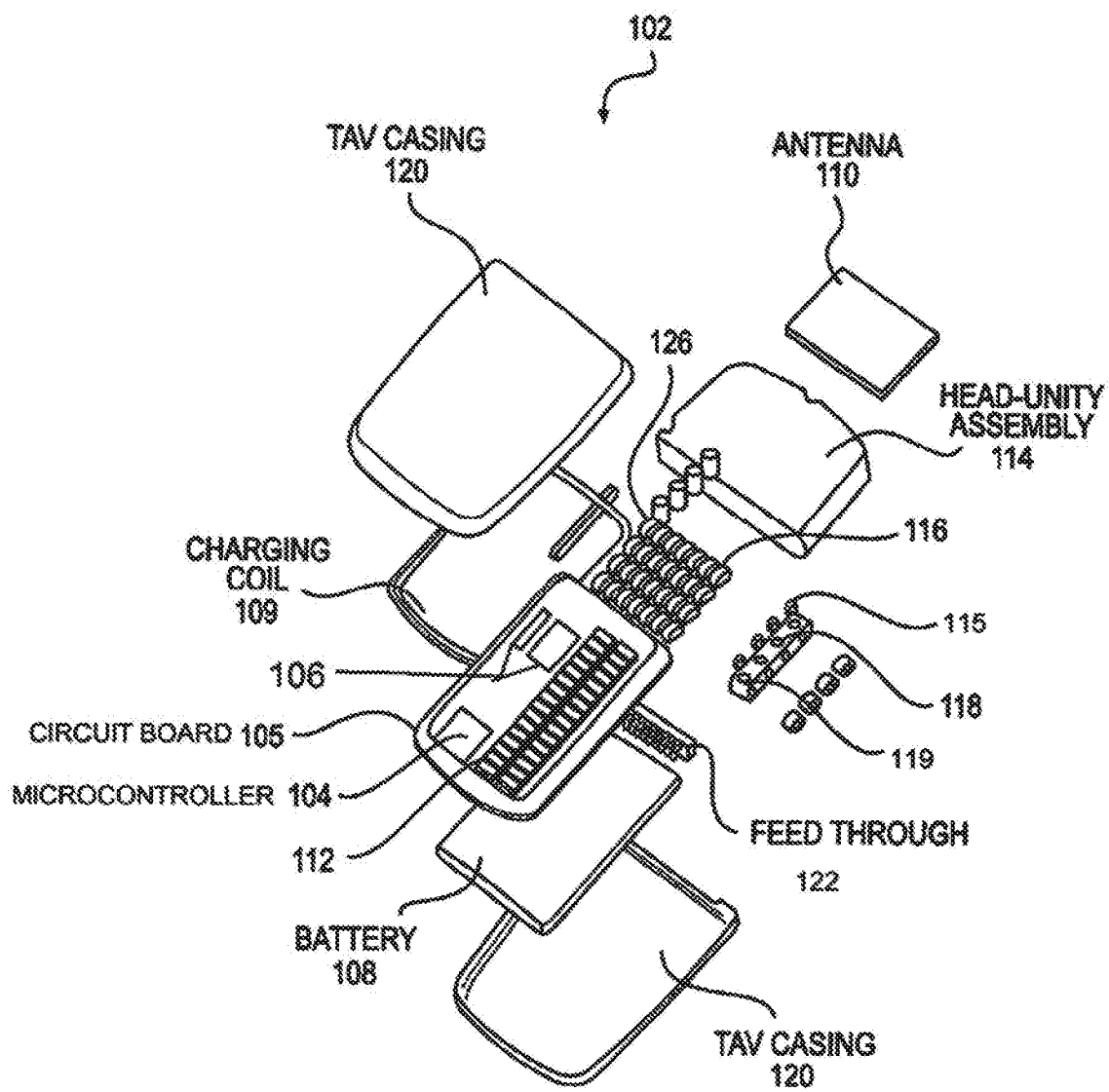
FIG. 2 depicts an exploded view of an implantable pulse generator (IPG) assembly, according to an embodiment.

FIG. 2 depicts an exploded view of an IPG 102. The IPG 102 consists of two major active components 104, 106, a battery 108, antenna 110, some support circuitry, and a multitude of output capacitors 112. The first of the major active components is the microcontroller 104 transceiver 104. It is responsible for receiving, decoding, and execution both commands and requests from the external remote. If necessary it passes these commands or requests onto the second major component, the ASIC 106. The ASIC 106 receives the digital data from the microcontroller 104 and performs the entire signal processing to generate the signals necessary for stimulation. These signals are then passed onto the stimulation electrodes 130 in the epidural space.

The ASIC 106 is comprised of a digital section and an analog section. The digital section is divided into multiple sections including; Timing Generators, Arbitration Control, Pulse Burst Conditioner, and Electrode Logic. The analog section receives the incoming pulses from the digital section and amplifies them in order to deliver the correct therapy. There are also a multitude of digital register memory elements that each section utilizes, both digital and analog.

The digital elements in the ASIC 106 are all made up of standard subsets of digital logic including logic gates, timers, counters, registers, comparators, flip-flips, and decoders. These elements are ideal for processing the stimulation pulses as all of them can function extremely fast-orders of magnitudes faster than the required pulse width. The elements all function at one single voltage, usually 5.0, 3.3, 2.5, or 1.8 volts.

The timing generators are the base of each of the stimulation sets. It generates the actual rising and falling edge triggers for each phase of the bi-phasic pulse. It accomplishes this by taking the incoming clock that is fed from the microcontroller 104 and feeding it into a counter. For the purpose of this discussion, assume the counter simply counts these rising clock edges infinitely. The output of the counter is fed into six different comparators. The comparators other input is connected to specific registers that are programmed by the microcontroller 104. When the count equals the value stored in the register, the comparator asserts a positive signal.

The first comparator is connected to the SET signal of a SR flip flop. The SR flip flop stays positive until the RESET signal is asserted, which the second comparator is connected to. The output of the SR flip flop is the first phase of the bi-phasic pulse. Its rising & falling edges are values stored in the registers and programmed by the microcontroller 104. The third and fourth comparators & registers work in exactly the same way to produce the second phase of the bi-phasic pulse using the second SR flip flop.

The fifth comparator is connected the RESET of the final SR-Flip flop in the timing generator. This flip flop is SET by the first comparator, which is the rising edge of the first pulse. The RESET is then triggered by the value the microprocessor programmed into the register connected to the comparator. This allows for a 'holdoff' period after the falling edge of the second pulse. The output of this third SR flip flop can be thought of as an envelope of the biphasic pulses indicating when this particular timing generator is active.

The final comparator of the system is once again connected to a register that stores the frequency values from the microprocessor. Essentially when the count reaches this value it triggers the comparator which is fed back to the counter to reset it to zero and beginning the entire pulse generation cycle again. The ASIC 106 may contain many of these timing generators as each can control anywhere from two to all of the electrodes 130 connected to the IPG 102 at a time. However, when there is more than one timing generator and multiple channels have been actively programmed then there needs to be a mechanism for suppressing a second channel from turning on when another is already active.

The next circuit block contained in the IPG 102 is the arbitrator. The arbitrator functions by looking at each of the timing generators' envelope signals and makes sure only one can be active at a time. If a second tries to activate then the arbitrator suppresses that signal.

The arbitrator accomplishes this by bringing each of the channel envelope signals into a rising edge detection circuit. Once one is triggered it is fed into the SET pin of an SR flip flop. The output of this SR-flip flop is fed into all of the other rising edge detectors in order to suppress them from triggering. The channel envelope signal is also fed into a falling-edge detector which is then fed into the RESET of the same SR flip flop. The output of the SR flip flops are then connected to switches whose outputs are all tied together that turn on/off that channels particular biphasic pulse train. Therefore, the output of this circuit element is a single bi-phasic pulse train and a signal designating which timing generator that particular pulse train is sourced from. Essentially, the circuit looks for a channel to go active. Once it finds one it suppresses all others until that channel becomes inactive.

The next section of the circuit works very similarly to the timing generators to create a high speed burst pulse train that is then combined with the stimulation pulse train to create a bursted bi-phasic pulse train if desired.

It accomplishes this by taking the incoming clock that is fed from the microcontroller 104 and feeding it into a counter. The counter can count these rising clock edges infinitely. The counter is only active during a single phase of the bi-phasic signal and begins counting as soon as the rising edge is detected. The output of the counter is fed into a comparator, along with a microcontroller-programmed register, whose output is connected to the reset pin on the counter. Therefore, this counter will simply count to a programmed value and reset. This programmed value is the burst frequency.

The output of the comparator is then fed into an edge detection circuit and then a flip flop that combines it with the actual stimulation pulse train to create a single phase bursted stimulation pulse. The entire circuit is duplicated for the second phase of the signal resulting in the desired bursted bi-phasic pulse train. The stimulation signal is now handed over to the electrode logic stage.

The electrode logic conditions and directs the bi-phasic signals to the analog section of the ASIC 106. At this point, the bi-phasic signals contain all of the pertinent timing information, but none of the required amplitude information. The incoming signals include the bi-phasic pulse train and another signal designating which timing generator the current active train came from. Each electrode logic cell has a register for each timing generator that stores this particular electrode's 130 amplitude values for that timing generator. The electrode logic cell uses the designation signal to determine which register to pull the amplitude values from, e.g. if the third timing generator is passed through the arbitration circuit then the electrode logic would read the value from the third register.

Once the value is pulled from the register, it goes through a series of logic gates. The gates first determine that the electrode 130 should be active. If not, no further action is taken and the analog section of the electrode output is not activated, thereby saving precious battery 108 power. Next, a determination is made if the particular electrode 130 is an anode or cathode. If the electrode is deemed to be an anode, the electrode logic passes the amplitude information and the biphasic signal to the positive current (digital to analog converter) DAC in the analog section of the ASIC 106. If the electrode is deemed to be a cathode, the electrode logic passes the amplitude information and the biphasic signal to the negative current DAC in the analog section of the ASIC 106. The electrode logic circuit must make these decisions for each phase of the bi-phasic signal as every electrode 130 will switch between being an anode and a cathode.

The analog elements in the ASIC 106 are uniquely designed in order to produce the desired signals. The basis of analog IC design is the field effect transistor (FET) and the type of high current multiple output design required in SCS 100 means that the bulk of the silicon in the ASIC 106 will be dedicated to the analog section.

The signals from the electrode output are fed into each current DAC when that specific electrode 130 should be activated. Each electrode 130 has a positive and a negative current DAC, triggered by the electrode logic and both are never active at the same time. The job of each current DAC is, when activated, to take the digital value representing a stimulation current amplitude and produce an analog representation of this value to be fed into the output stage.

This circuit forms half of the barrier between the digital and analog sections of the ASIC 106.

The digital section of the ASIC 106 is built upon a technology that only allows small voltages to exist. In moving to the analog section, the output of the current DAC (which is a low level analog signal) must be amplified to a higher voltage for use in the analog section. The circuit that performs this task is called a power level shifter. Because this circuit is built upon two different manufacturing technologies and requires high precision analog circuits built upon a digital base, it can be difficult to implement.

Once the voltages have been converted for usage in the analog portion of the ASIC 106 the voltages are passed on to the output current stages. There are two current sources per electrode output. One will source a positive current and one will sink a negative current, but both will never be active simultaneously. The current sources themselves are made up of analog elements similar to a Howland current source. There is an input stage, and an amplification stage with feedback through a sensing component to maintain the constant current. The input stage takes the analog voltage values from the power level shifter and produces an output pulse designated for the amplifier. The amplifier then creates the pulses of varying voltages but constant current flow. The sources are capable of sourcing or sinking up to 12.7 mA at 0.1 mA resolution into a load of up to 1.2 k Ohms. This translates into range of 15 volts, which will vary depending on the load in order to keep the current constant.

The microcontroller 104 to ASIC 106 interface is designed to be as simple as possible with minimal bus 'chatter' in order to save battery 108 life. The ASIC 106 can be a collection of registers programmed via a standard I$^2$C or SPI bus. Since the ASIC 106 is handling all the power management, there will also be a power good (PG) line between the two chips 104, 106 in order to let the microcontroller 104 know when it is safe to power up. The ASIC 106 will also need to use a pin on the microcontroller 104 in order to generate a hardware interrupt in case anything goes awry in the ASIC 106. The final connection is the time base for all of the stimulation circuitry. The ASIC 106 will require two clocks, one for its internal digital circuitry which will be fed directly from the microcontroller 104 clock output, and one to base all stimulation off of which will need to be synthesized by the microcontroller 104 and fed to the ASIC 106. All commands and requests to the ASIC 106 will be made over the I²C or SPI bus and will involve simply reading a register address or writing to a register. Even when the ASIC 106 generates a hardware interrupt, it will be the responsibility of the microcontroller 104 to poll the ASIC 106 and determine the cause of the interrupt.

The wireless interface is based upon the FCCs MedRadio standard operating in the 402-405 MHz range utilizing up to 10 channels for telemetry. The protocol implemented is chosen to minimize transmission and maximize battery 108 life. All processing will take place on the user remote/programmer and the only data transmitted is exactly what will be used in the microcontroller 104 to ASIC 106 bus. That is, all of the wireless packets will contain necessary overhead information along with only a register address, data to store in the register, and a command byte instructing the microcontroller 104 what to do with the data. The overhead section of the wireless protocol will contain synchronization bits, start bytes, an address which is synchronized with the IPG's 102 serial number, and a CRC byte to assure proper transmission. The packet length is kept as small as possible in order to maintain battery 108 life. Since the IPG 102 cannot listen for packets all the time due to battery 108 life, it cycles on for a duty cycle of less than 0.05% of the time. This time value can be kept small as long as the data packets are also small. The user commands needed to run the system are executed by the entire system using flows.

The IPG 102 uses an implantable grade Li ion battery 108 with 215 mAHr with zero volt technology. The voltage of the battery 108 at full capacity is 4.1 V and it supplies current only until it is drained up to 3.3 V which is considered as 100% discharged. The remaining capacity of the battery 108 can be estimated at any time by measuring the voltage across the terminals. The maximum charge rate is 107.5 mA. A Constant Current, Constant Voltage (CCCV) type of regulation can be applied for faster charging of the battery 108.

The internal secondary coil 109 is made up of 30 turns of 30 AWG copper magnet wires. The ID, OD, and the thickness of the coil are 30, 32, and 2 mm, respectively. Inductance L2 is measured to be 58 uH, a 80 nF capacitor is connected to it to make a series resonance tank at 74 kHz frequency. In the art of induction charging, two types of rectifiers are considered to convert the induced AC into usable DC, either a bridge full wave rectifier or a voltage doubler full wave rectifier. To obtain a higher voltage, the voltage double full wave rectifier is used in this application. The rectifier is built with high speed Schottky diodes to improve its function at high frequencies of the order 100 kHz. A Zener diode and also a 5V voltage regulator are used for regulation. This circuit will be able to induce AC voltage, rectify to DC, regulate to 5V and supply 100 mA current to power management IC that charges the internal battery 108 by CCCV regulation.

The regulated 5V 100 mA output from the resonance tank is fed to, for example, a Power Management Integrated Circuit (PMIC) MCP73843. This particular chip was specially designed by Microchip to charge a Li ion battery 108 to 4.1 V by CCCV regulation. The fast charge current can be regulated by changing a resistor; it is set to threshold current of 96 mA in the example circuit. The chip charges the battery 108 to 4.1 V as long as the current received is more than 96 mA. However, if the supply current drops below 96 mA, it stops to charge the battery 108 until the supply is higher than 96 again. For various practical reasons, if the distance between the coils increases, the internal secondary coil 109 receives lesser current than the regulated value, and instead of charging the battery 108 slowly, it pauses the charging completely until it receives more than 96 mA. It is understood to those with skill in the art that other power management chips can be used and the power management chip is not limited to the PMIC MCP738432 chip.

All the functions of the IPG 102 are controlled from outside using a hand held remote controller specially designed for this device. Along with the remote control, an additional control is desirable to operate the IPG 102 if the remote control was lost or damaged. For this purpose, a Hall effect based magnet switch was incorporated to either turn ON or turn OFF the IPG 102 using an external piece of magnet. Magnet switch acts as a master control for the IPG 102 to turn on or off. A south pole of sufficient strength turns the output on and a north pole of sufficient strength turns the output off. The output is latched so that the switch continues to hold the state even after the magnet is removed from its vicinity.

The IPG 102 is an active medical implant that generates an electrical signal that stimulates the spinal cord. The signal is carried through a stimulation lead 140 that plugs directly into the IPG 102. The IPG 102 recharges wirelessly through an induction coil 109, and communicates via RF radio antenna 110 to change stimulation parameters. The IPG 102 is implanted up to 3 cm below the surface of the skin and can be fixed to the fascia by passing two sutures through holes in the epoxy header 114. The leads 140 are electrically connected to the IPG 102 through a lead contact system 116, a cylindrical spring-based contact system with inter-contact silicone seals. The leads 140 are secured to the IPG 102 with a set screw 117 that actuates within locking housing 118. Set screw compression on the lead's 140 fixation contact can be governed by a disposable torque wrench. The wireless recharging is achieved by aligning the exterior induction coil on the charger with the internal induction coil 109 within the IPG 102. The RF antenna within the remote's dongle 200 communicates with the RF antenna 110 in the IPG's 102 epoxy header 114. FIG. 2 illustrates an exploded view of the IPG 102 assembly.

Figure 3:
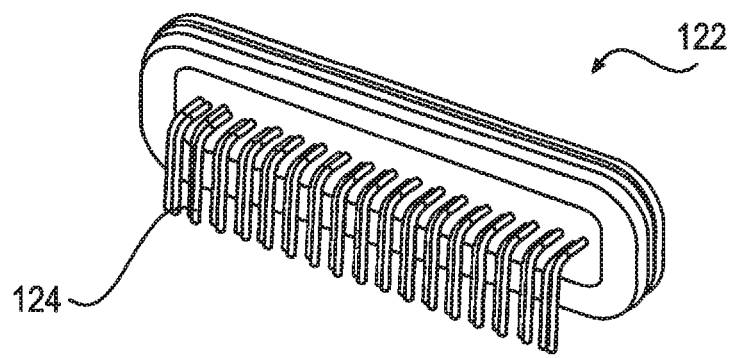
FIG. 3 depicts a feedthrough assembly of an implantable pulse generator (IPG) assembly, according to an embodiment.
Figure 6:
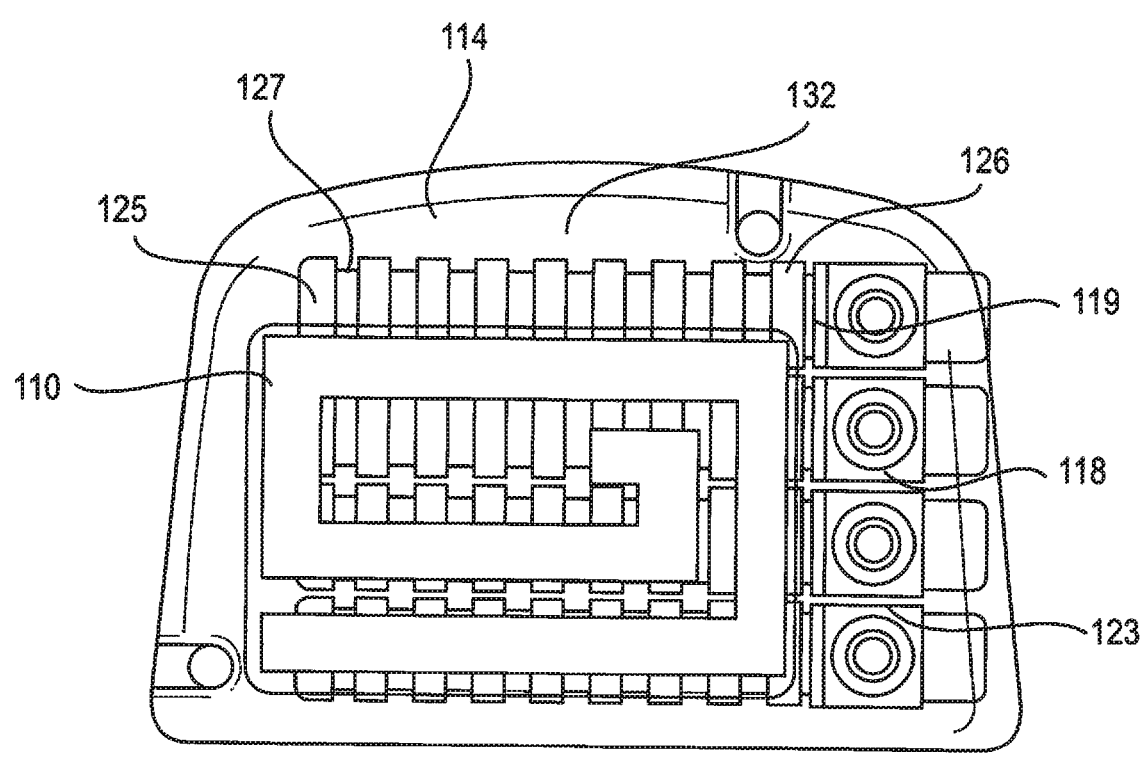
FIG. 6 depicts a head unit assembly of an implantable pulse generator (IPG) assembly, according to an embodiment.
Figure 7:
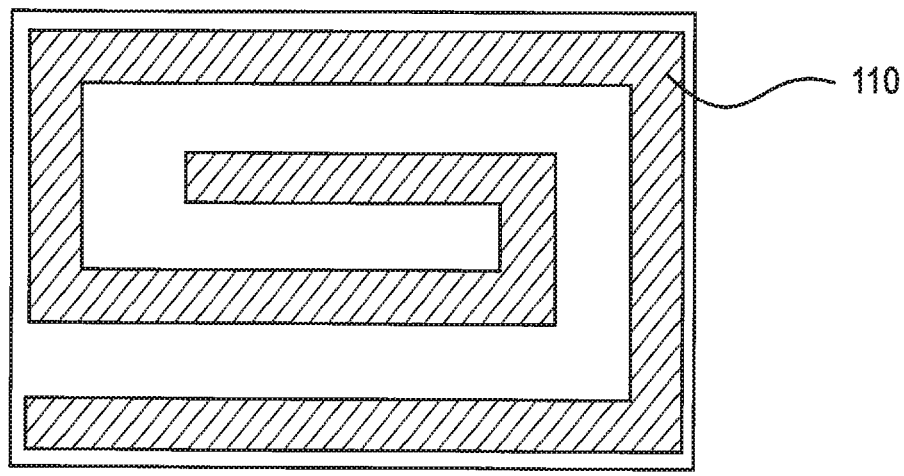
FIG. 7 depicts an RF antenna of an implantable pulse generator (IPG) assembly, according to an embodiment.

The IPG 102 is an assembly of a hermetic titanium (6 Al-4V) casing 120 which houses the battery 108, circuitry 104, 106, and charging coil 109. The IPG 102 further includes an epoxy header 114 (see FIG. 6), which houses the lead contact assembly 116, locking housing 118, and RF antenna 110 (see FIGS. 6 and 7). The internal electronics are connected to the components within the epoxy head through a hermetic feedthrough 122, as shown in FIG. 3. The feedthrough 122 is a titanium (6 Al-4V) flange with an alumina window and gold trimming. Within the alumina window are thirty-four platinum-iridium (90-10) pins that interface internally with a direct solder to the circuit board, and externally with a series of platinum iridium wires laser-welded to the antenna 110 and lead contacts 126. The IPG 102 interfaces with 32 electrical contacts 126, which are arranged in four rows of eight contacts 126. Thirty two of the feedthrough's 122 pins 124 interface with the contacts 126, while two interface with the antenna 110, one to the ground plane and one to the antenna 110 feed.

Figure 4:
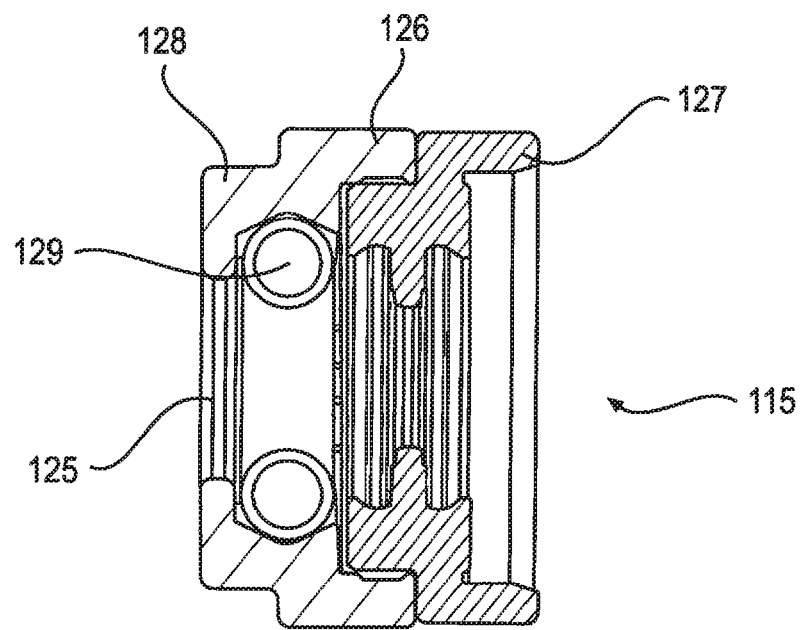
FIG. 4 depicts a lead contact system of an implantable pulse generator (IPG) assembly, according to an embodiment.
Figure 5:
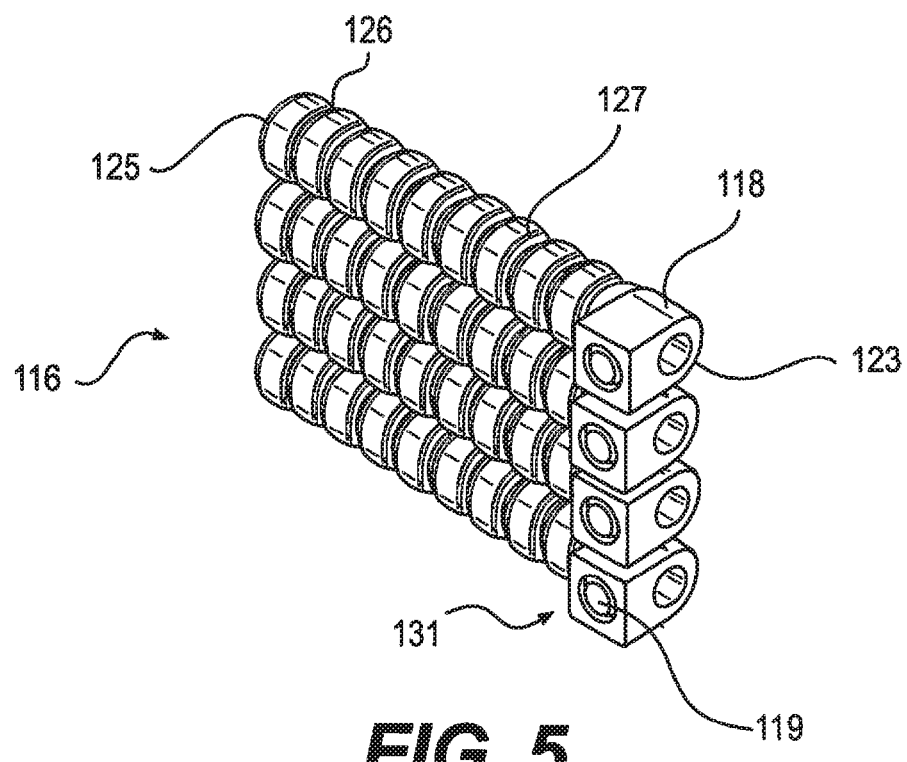
FIG. 5 depicts a lead contact assembly of an implantable pulse generator (IPG) assembly, according to an embodiment.

FIGS. 4 and 5 depict a lead contact system 115 and assembly 116, respectively. The lead contacts 126 consist of an MP35N housing 128 with a platinum-iridium 90-10 spring 129. Each contact 126 is separated by a silicone seal 127. At the proximal end of each stack of 8 contacts 126 is a titanium (6 Al-4V) cap 125 which acts as a stop for the lead 140. At the distal end is a titanium (6 Al-4V) set screw 119 and block 118 for lead fixation. At the lead entrance point is a silicone tube 123 which provides strain relief as the lead 140 exits the head unit 114, and above the set screw 119 another silicone tube 131 with a small internal canal allows the torque wrench to enter but does not allow the set screw 119 to back out. In addition to the contacts 126 and antenna 110, the header 114 also contains a radiopaque titanium (6 A1-4V) tag 132 which allows for identification of the device under fluoroscopy. The overmold of the header 114 is Epotek 301, a two-part, biocompatible epoxy. FIGS. 4, 5, 6, and 7 depict illustrations of lead contact system 115, lead contact assembly 116, head unit assembly 114, and RF antenna 110, respectively.

Internal to the titanium (6 A1-4V) case 120 are the circuit board 105, battery 108, charging coil 109, and internal plastic support frame. The circuit board 105 can be a multi-layered FR-4 board with copper traces and solder mask coating. Non-solder masked areas of the board can be electroless nickel immersion gold. The implantable battery 108, all surface mount components, ASIC 106, microcontroller 104, charging coil 109, and feedthrough 122 will be soldered to the circuit board 105. The plastic frame, made of either polycarbonate or ABS, will maintain the battery's 108 position and provide a snug fit between the circuitry 105 and case 120 to prevent movement. The charging coil 109 is a wound coated copper.

Leads

Figure 8:
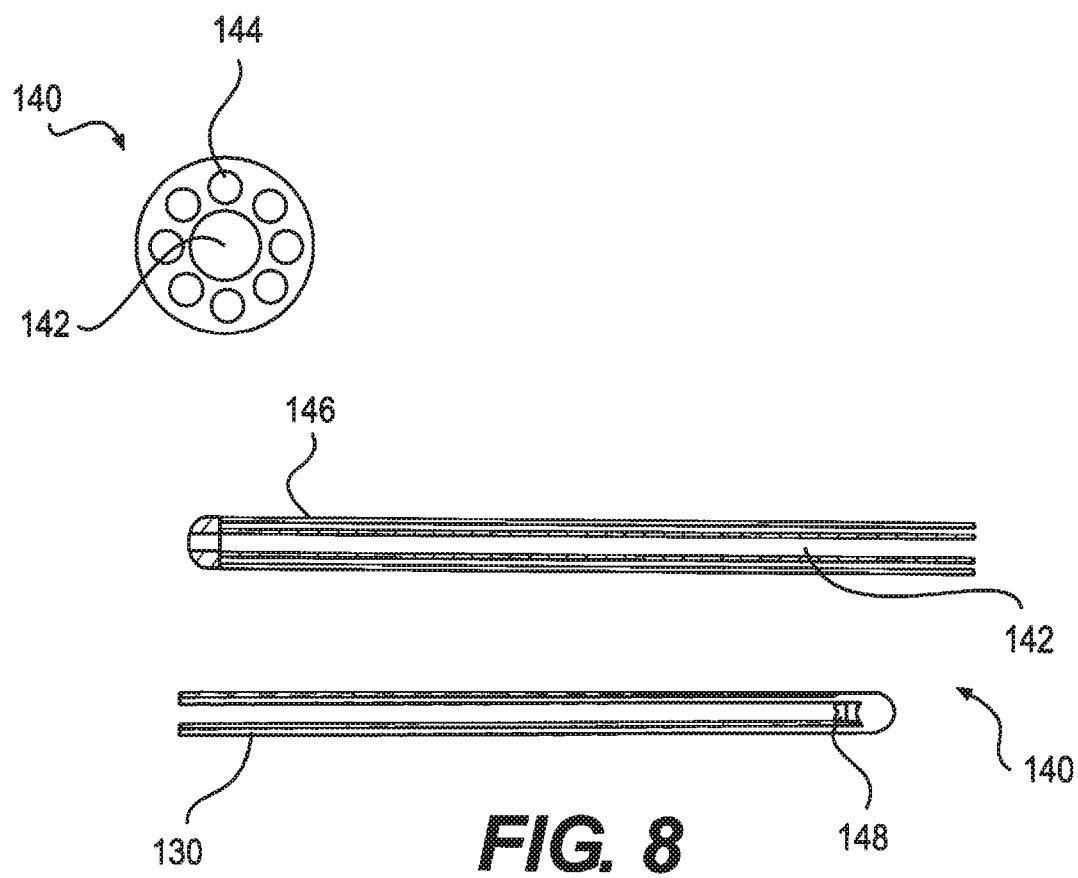
FIG. 8 depicts a percutaneous lead, according to an embodiment.

The percutaneous stimulation leads 140, as depicted in FIG. 8, are a fully implantable electrical medical accessory to be used in conjunction with the implantable SCS 100. The primary function of the lead is to carry electrical signals from the IPG 102 to the target stimulation area on the spinal cord. Percutaneous stimulation leads 140 provide circumferential stimulation. The percutaneous stimulation leads 140 provide a robust, flexible, and bio- compatible electric connection between the IPG 102 and stimulation area. The leads 140 are surgically implanted through a spinal needle, or epidural needle, and are driven through the spinal canal using a steering stylet that passes through the center of the lead 140. The leads 140 are secured mechanically to the patient using either an anchor or a suture passed through tissue and tied around the body of the lead 140. The leads 140 are secured at the proximal end with a set-screw 119 on the IPG 102 which applies radial pressure to a blank contact on the distal end of the proximal contacts.

The percutaneous stimulation leads 140 consist of a combination of implantable materials. Stimulation electrodes 130 at the distal end and electrical contacts at the proximal end are made of a 90-10 platinum-iridium alloy. This alloy is utilized for its bio-compatibility and electrical conductivity. The electrodes 130 are geometrically cylindrical. The polymeric body of the lead 140 is polyurethane, chosen for its bio-compatibility, flexibility, and high lubricity to decrease friction while being passed through tissue. The polyurethane tubing has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP3SN strands with a 28% silver core. The wires 146 are individually coated with ethylene tetrafluoroethylene (ETFE), to provide an additional non-conductive barrier. The wires 146 are laser welded to the contacts and electrodes 130, creating an electrical connection between respective contacts on the proximal and distal ends. The leads 140 employ a platinum-iridium plug 148, molded into the distal tip of the center lumen 142 to prevent the tip of the steering stylet from puncturing the distal tip of the lead 140. Leads 140 are available in a variety of 4 and 8 electrode 130 configurations. These leads 140 have 4 and 8 proximal contacts (+1 fixation contact), respectively. Configurations vary by electrode 130 number, electrode 130 spacing, electrode 130 length, and overall lead 140 length.

Figure 9:
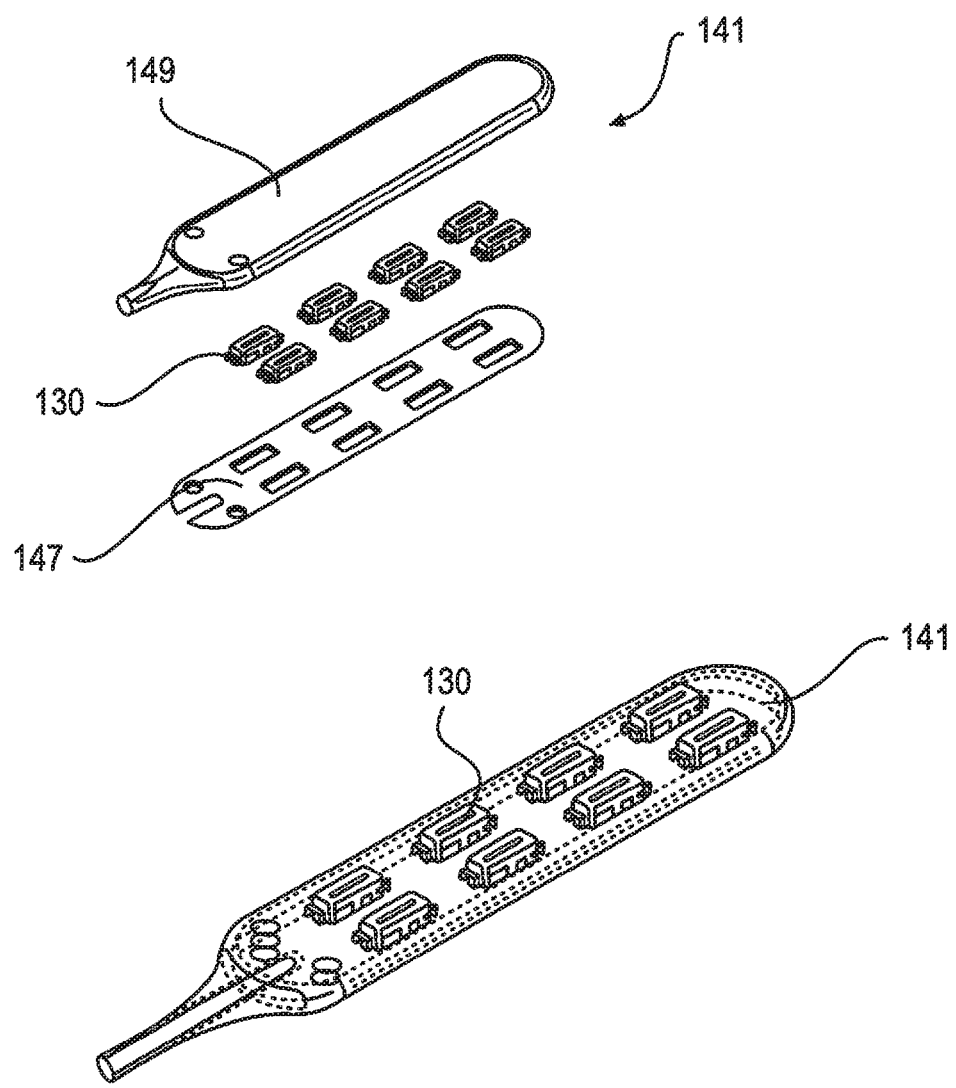
FIG. 9 depicts a paddle lead, according to an embodiment.

The paddle stimulation leads 141, as depicted in FIG. 9, are a fully implantable electrical medical accessory to be used in conjunction with the implantable SCS 100. The primary function of the paddle lead 141 is to carry electrical signals from the IPG 102 to the target stimulation area on the spinal cord. The paddle leads 141 provide uni-direction stimulation across a 2-dimensional array of electrodes 130, allowing for greater precision in targeting stimulation zones. The paddle stimulation leads 141 provide a robust, flexible, and bio-compatible electric connection between the IPG 102 and stimulation area. The leads 141 are surgically implanted through a small incision, usually in conjunction with a laminotomy or laminectomy, and are positioned using forceps or a similar surgical tool. The leads 141 are secured mechanically to the patient using either an anchor or a suture passed through tissue and tied around the body of the lead 141. The leads 141 are secured at the proximal end with a set- screw on the IPG 102 which applies radial pressure to a fixation contact on the distal end of the proximal contacts.

The paddle stimulation leads 141 consist of a combination of implantable materials. Stimulation electrodes 130 at the distal end and electrical contacts at the proximal end are made of a 90-10 platinum-iridium alloy utilized for its bio-compatibility and electrical conductivity. The polymeric body of the lead 141 is polyurethane, chosen for its bio-compatibility, flexibility, and high lubricity to decrease friction while being passed through tissue. The polyurethane tubing has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP35N strands with a 28% silver core. The wires 146 are individually coated with ethylene tetrafluoroethylene (ETFE), to provide an additional non-conductive barrier. At the distal tip of the paddle leads 141 is a 2-dimensional array of flat rectangular electrodes 130 molded into a flat silicone body 149. In an embodiment, one side of the rectangular electrodes 130 is exposed, providing uni-directional stimulation. The wires 146 are laser welded to the contacts and electrodes 130, creating an electrical connection between respective contacts on the proximal and distal ends. Also molded into the distal silicone paddle is a polyester mesh 147 adding stability to the molded body 149 while improving aesthetics by covering wire 146 routing. The number of individual 8-contact leads 141 used for each paddle 141 is governed by the number of electrodes 130. Electrodes 130 per paddle 141 range from 8 to 32, split into between one and four proximal lead 141 ends. Each proximal lead 141 has 8 contacts (+1 fixation contact).

Configurations vary by electrode 130 number, electrode 130 spacing, electrode length, and overall lead length.

Figure 10:
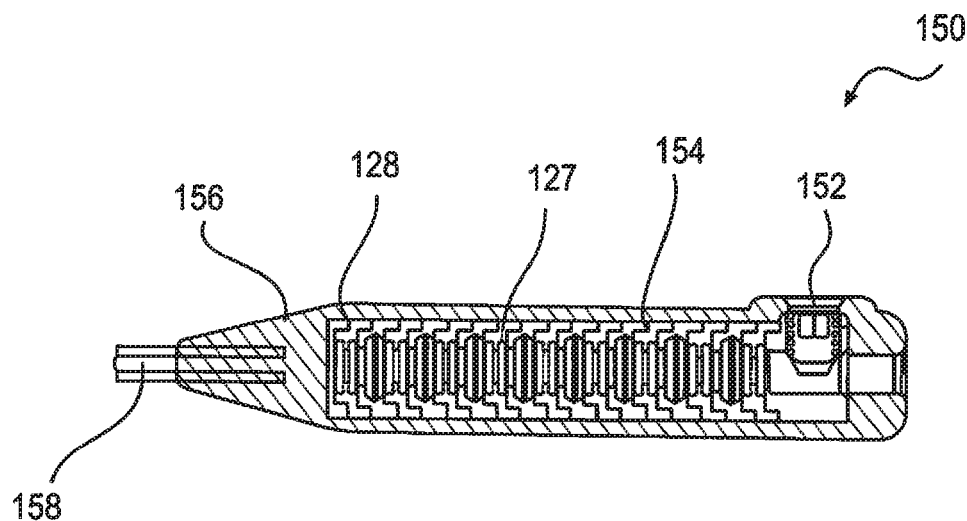
FIG. 10 depicts a lead extension, according to an embodiment.

The lead extensions 150, as depicted in FIG. 10, are a fully implantable electrical medical accessory to be used in conjunction with the implantable SCS 100 and either percutaneous 140 or paddle 141 leads. The primary function of the lead extension 150 is to increase the overall length of the lead 140, 141 by carrying electrical signals from the IPG 102 to the proximal end of the stimulation lead 140, 141. This extends the overall range of the lead 140, 141 in cases where the length of the provided leads 140, 141 are insufficient. The lead extensions 150 provide a robust, flexible, and bio-compatible electric connection between the IPG 102 and proximal end of the stimulation lead 140, 141. The extensions 150 may be secured mechanically to the patient using either an anchor or a suture passed through tissue and tied around the body of the extension 150. Extensions 150 are secured at the proximal end with a set-screw 119 on the IPG 102 which applies radial pressure to a fixation contact on the distal end of the proximal contacts of the extension 150. The stimulation lead 140, 141 is secured to the extension 150 in a similar fashion, using a set screw 152 inside the molded tip of extension 150 to apply a radial pressure to the fixation contact at the proximal end of the stimulation lead 140, 141.

The lead extension 150 consists of a combination of implantable materials. At the distal tip of the extension 150 is a 1×8 array of implantable electrical contacts 154, each consisting of MP35 housing 128 and 90-10 platinum-iridium spring. A silicone seal 127 separates each of the housings 128. At the proximal end of the contacts is a titanium (6 A14V) cap which acts as a stop for the lead, and at the distal tip, a titanium (6 A14V) block and set screw 152 for lead fixation. The electrical contacts at the proximal end are made of a 90-10 platinum-iridium alloy utilized for its bio-compatibility and electrical conductivity. The polymeric body 156 of the lead 150 is polyurethane, chosen for its bio-compatibility, flexibility, and high lubricity to decrease friction while being passed through tissue. The polyurethane tubing 158 has a multi- lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes. These wires 146 are a bundle of MP35N strands with a 28% silver core. The wires 146 are individually coated with ethylene tetrafluoroethylene (ETFE), to provide an additional non-conductive barrier. Each lead extension 150 has 8 proximal cylindrical contacts (+1 fixation contact).

Figure 11:
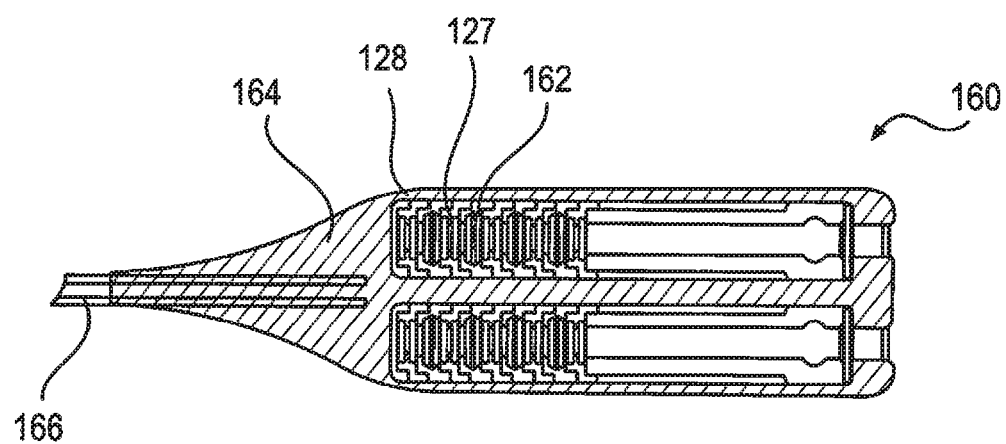
FIG. 11 depicts a lead splitter, according to an embodiment.

The lead splitter 160, as depicted in FIG. 11, is a fully implantable electrical medical accessory which is used in conjunction with the SCS 100 and typically a pair of 4-contact percutaneous leads 140. The primary function of the lead splitter 160 is to split a single lead 140 of eight contacts into a pair of 4 contact leads 140. The splitter 160 carries electrical signals from the IPG 102 to the proximal end of two 4-contact percutaneous stimulation leads 140. This allows the surgeon access to more stimulation areas by increasing the number of stimulation leads 140 available. The lead splitter 160 provides a robust, flexible, and bio-compatible electrical connection between the IPG 102 and proximal ends of the stimulation leads 140. The splitters 160 may be secured mechanically to the patient using either an anchor or a suture passed through tissue and tied around the body of the splitter 160. Splitters 160 are secured at the proximal end with a set-screw 119 on the IPG 102 which applies radial pressure to a fixation contact on the distal end of the proximal contacts of the splitter 160. The stimulation leads 140 are secured to the splitter 160 in a similar fashion, using a pair of set screws inside the molded tip of splitter 160 to apply a radial pressure to the fixation contact at the proximal end of each stimulation lead 140.

The lead splitter 160 consists of a combination of implantable materials. At the distal tip of the splitter 160 is a 2×4 array of implantable electrical contacts 162, with each contact 162 consisting of MP35 housing 128 and 90-10 platinum-iridium spring. A silicone seal 127 separates each of the housings 128. At the proximal end of each row of contacts 162 is a titanium (6 A14V) cap which acts as a stop for the lead, and at the distal tip, a titanium (6 A14V) block and set screw for lead fixation. The electrical contacts at the proximal end of the splitter 160 are made of a 90-10 platinum-iridium alloy utilized for its bio-compatibility and electrical conductivity. The polymeric body 164 of the lead 160 is polyurethane, chosen for its bio-compatibility, flexibility, and high lubricity to decrease friction while being passed through tissue. The polyurethane tubing 166 has a multi-lumen cross section, with one center lumen 142 and eight outer lumens 144. The center lumen 142 acts as a canal to contain the steering stylet during implantation, while the outer lumens 144 provide electrical and mechanical separation between the wires 146 that carry stimulation from the proximal contacts to distal electrodes 130. These wires 146 are a bundle of MP3SN strands with a 28% silver core. The wires 146 are individually coated with ethylene tetrafluoroethylene (ETFE), to provide an additional non-conductive barrier. Each lead splitter 160 has 8 proximal contacts (+1 fixation contact), and 2 rows of 4 contacts 162 at the distal end.

Anchors

Figure 12:
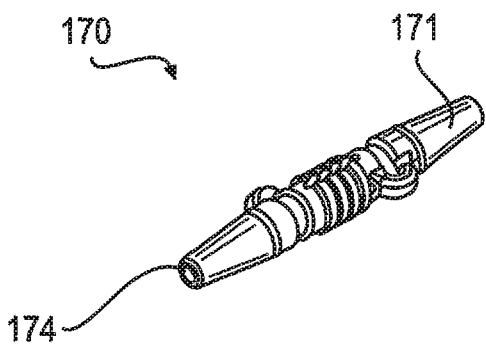
FIG. 12 depicts a sleeve anchor, according to an embodiment.
Figure 13:
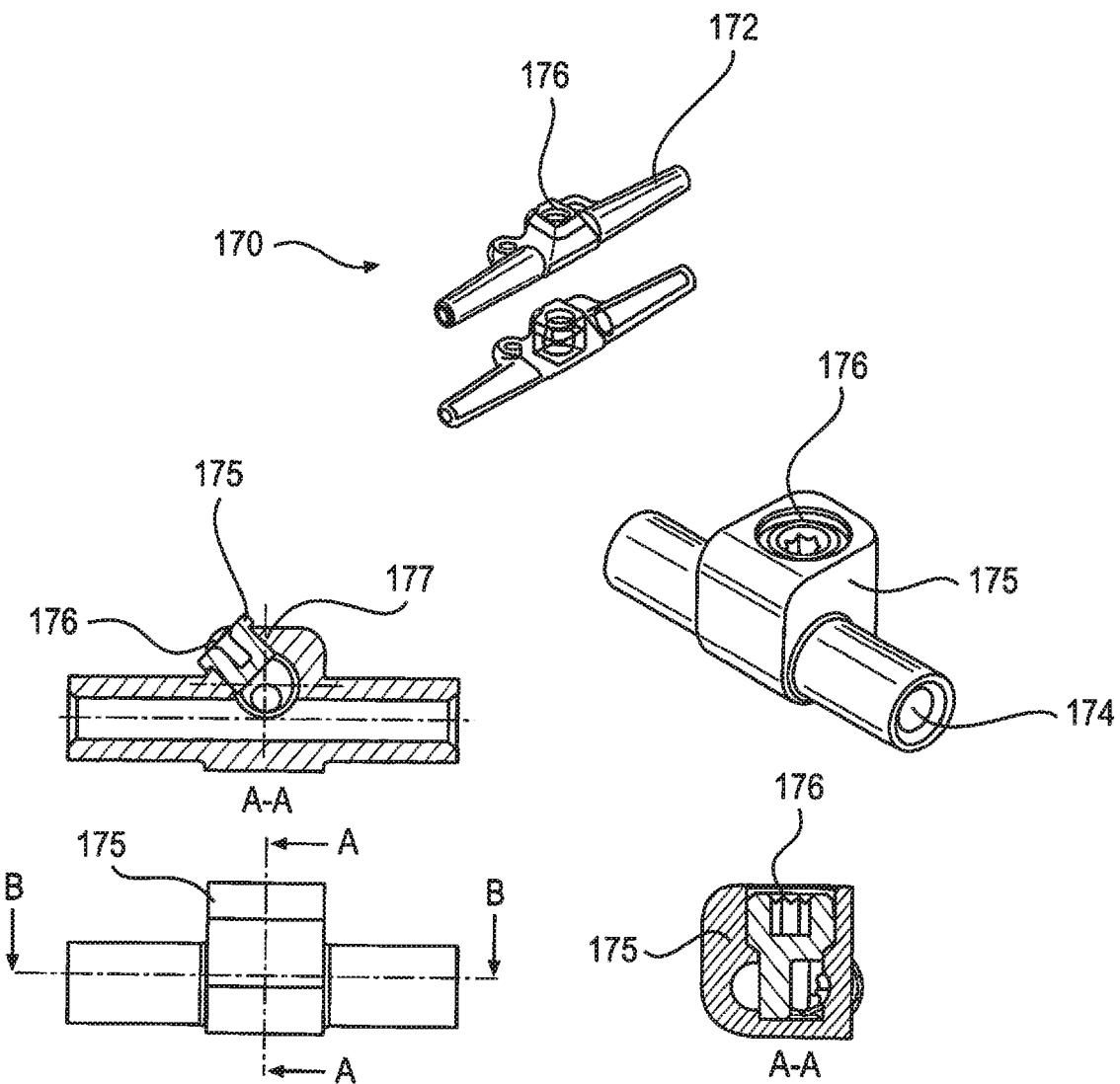
FIG. 13 depicts a mechanical locking anchor, according to an embodiment.

The lead anchor 170, as depicted in FIGS. 12 and 13, is a fully implantable electrical medical accessory which is used in conjunction with both percutaneous 140 and paddle 141 stimulation leads. The primary function of the lead anchor 170 is to prevent migration of the distal tip of the lead 140, 141 by mechanically locking the lead 140, 141 to the tissue. There are currently two types of anchors 170, a simple sleeve 171, depicted in FIG. 12, and a locking mechanism 172, depicted in FIG. 13, and each has a slightly different interface. For the simple sleeve type anchor 171, the lead 140, 141 is passed through the center thru-hole 174 of the anchor 171, and then a suture is passed around the outside of the anchor 171 and tightened to secure the lead 140, 141 within the anchor 171. The anchor 171 can then be sutured to the fascia. The locking anchor 172 uses a set screw 176 for locking purposes, and a bi-directional disposable torque wrench for locking and unlocking. Tactile and audible feedback is provided for both locking and unlocking.

Both anchors 171, 172 can be molded from implant-grade silicone, but the locking anchor 172 uses an internal titanium assembly for locking. The 3-part mechanism is made of a housing 175, a locking set screw 176, and a blocking set screw 177 to prevent the locking set screw from back out. All three components can be titanium (6A14V). The bi-directional torque wrench can have a plastic body and stainless steel hex shaft.

Wireless Dongle

Figure 14:
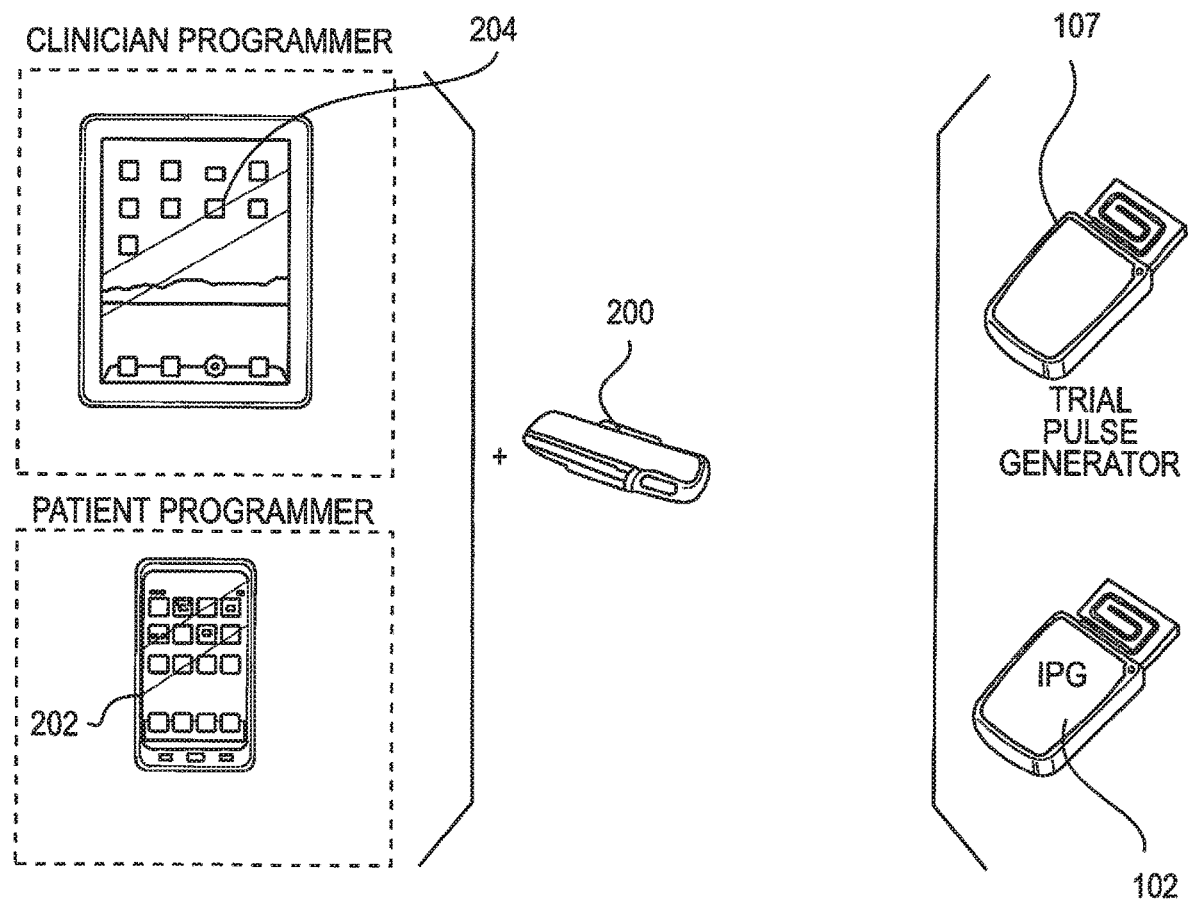
FIG. 14 illustrates communication via a wireless dongle with a tablet/clinician programmer and smartphone/mobile/patient programmer during trial and/or permanent implantation, according to an embodiment.

The wireless dongle 200 is the hardware connection to a smartphone/mobile 202 or tablet 204 that allows communication between the trial generator 107 or IPG 102 and the smartphone/mobile device 202 or tablet 204, as illustrated in FIG. 14. During the trial or permanent implant phases, the wireless dongle 200 is connected to the tablet 204 through the tablet 204 specific connection pins and the clinician programmer software on the tablet 204 is used to control the stimulation parameters. The commands from the clinician programmer software are transferred to the wireless dongle 200 which is then transferred from the wireless dongle 200 using RF signals to the trial generator 107 or the IPG 102. Once the parameters on the clinician programmers have been set, the parameters are saved on the tablet 204 and can be transferred to the patient programmer software on the smartphone/mobile device 202. The wireless dongle 200 is composed of an antenna, a microcontroller (having the same specifications as the IPG 102 and trial generator 107), and a pin connector to connect with the smartphone/mobile device 202 and the tablet 204.

Charger

The IPG 102 has a rechargeable lithium ion battery 108 to power its activities. An external induction type charger 210 (FIG. 1) wirelessly recharges the included battery 108 inside the IPG 102. The charger 210 is packaged into a housing and consists of a rechargeable battery, a primary coil of wire and a printed circuit board (PCB) containing the electronics. In operation, charger 210 produces a magnetic field and induces voltage into the secondary coil 109 in the IPG 102. The induced voltage is then rectified and used to charge the battery 108 inside the IPG 102. To maximize the coupling between the coils, both internal and external coils are combined with capacitors to make them resonate at a particular common frequency. The coil acting as an inductor L forms an LC resonance tank. The charger uses a Class-E amplifier topology to produce the alternating current in the primary coil around the resonant frequency. The charger 210 features include, but are not limited to:

Charge IPG 102 wirelessly

Charge up to a maximum depth of 30 mm

Integrated alignment sensor indicates alignment between the charger and IPG 102 resulting in higher power transfer efficiency Alignment sensor provides audible and visual feedback to the user Compact and Portable A protected type of cylindrical Li ion battery is used as the charger 210 battery. A Class- E power amplifier topology is a much used type of amplifier for induction chargers, especially for implantable electronic medical devices. Due to the Class-E power amplifier's relatively high theoretical efficiency it is often used for devices where high efficiency power transfer is necessary. A 0.1 ohm high wattage resistor is used in series to sense the current through this circuit.

The primary coil L1 is made by 60 turns of Litz wire type 100/44–100 strands of 44 AWG each. The Litz wire solves the problem of skin effect and keeps its impedance low at high frequencies. Inductance of this coil was initially set at 181 uH, but backing it with a Ferrite plate increases the inductance to 229.7 uH. The attached ferrite plate focuses the produced magnetic field towards the direction of the implant. Such a setup helps the secondary coil receive more magnetic fields and aids it to induce higher power.

When the switch is ON, the resonance is at frequency $$f = \frac{1}{2\pi\sqrt{L1C2}}$$

When the switch is OFF, it shifts to $$f = \frac{1}{2\pi\sqrt{L1\frac{C1C2}{C1+C2}}}$$

In a continuous operation the resonance frequency will be in the range $$\frac{1}{2\pi\sqrt{L1C2}} < f < \frac{1}{2\pi\sqrt{L1\frac{C1C2}{C1+C2}}}$$

To make the ON and OFF resonance frequencies closer, a relatively larger value of C1 can be chosen by a simple criteria as follows C1=nC2; a value of n=4 was used in the example above; in most cases 3<n<10.

The voltages in these Class-E amplifiers typically go up to the order of 300 VAC. Capacitors selected must be able to withstand these high voltages, sustain high currents and still maintain low Effective Series Resistance (ESR). Higher ESRs result in unnecessary power losses in the form of heat. The circuit is connected to the battery through an inductor which acts as a choke. The choke helps to smoothen the supply to the circuit. The N Channel MOSFET acts as a switch in this Class-E power amplifier. A FET with low ON resistance and with high drain current Id is desirable.

In summary, the circuit is able to recharge the IPG 102 battery 108 from 0to 100% in approximately two hours forty-five minutes with distance between the coils being 29 mm. The primary coil and the Class-E amplifier draws DC current of 0.866 A to achieve this task. To improve the efficiency of the circuit, a feedback closed loop control is implemented to reduce the losses. The losses are minimum when the MOSFET is switched ON and when the voltage on its drain side is close to zero.

The controller takes the outputs from operational amplifiers, checks if the outputs meet the criteria, then triggers the driver to switch ON the MOSFET for the next cycle. The controller can use a delay timer, an OR gate and a 555 timer in monostable configuration to condition the signal for driver. When the device is switched ON, the circuit will not function right away as there is no active feedback loop. The feedback becomes active when the circuit starts to function. To provide an active feedback loop, an initial external trigger is applied to jump start the system.

Alignment Sensor

The efficiency of the power transfer between the external charger 210 and the internal IPG 102 will be maximum only when the charger 210 and IPG 102 are properly aligned. An alignment sensor is provided to ensure proper alignment as part of the external circuit design and is based on the principle of reflected impedance. When the external coil is brought closer to the internal coil, the impedance of both circuits change. The sensing is based on measuring the reflected impedance and testing whether it crosses the threshold. A beeper provides an audible feedback to the patient and a LED provides visual feedback.

When the impedance of the circuit changes, the current passing through it also changes. A high power 0.1 ohm resistor can be used in the series of the circuit to monitor the change in current. The voltage drop across the resistor is amplified 40 times and then compared to a fixed threshold value using an operational amplifier voltage comparator. The output is fed to a timer chip which in turn activates the beeper and LED to provide feedback to the user.

The circuit can sense the alignment up to a distance of approximately 30 mm. The current fluctuation in the circuit depends on more factors than reflected impedance alone and the circuit is sensitive to other parameters of the circuit as well. To reduce the sensitivity related to other parameters, one option is to eliminate interference of all the other factors and improve the functionality of the reflected impedance sensor—which is very challenging to implement within the limited space available for circuitry. Another option is to use a dedicated sensor chip to measure the reflected impedance.

A second design uses sensors designed for proximity detector or metal detectors for alignment sensing. Chips designed to detect metal bodies by the effect of Eddy currents on the HF losses of a coil can be used for this application. The TDE0160 is an example of such a chip.

The external charger is designed to work at 75 to 80 kHz, whereas the proximity sensor was designed for 1 MHz. The sensor circuit is designed to be compatible with the rest of the external and is fine tuned to detect the internal IPG 102 from a distance of approximately 30 mm.

Programmer

The Clinician Programmer is an application that is installed on a tablet 204. It is used by the clinician to set the stimulation parameters on the trial generator 107 or IPG 102 during trial and permanent implantation in the operating room. The clinician programmer is capable of saving multiple settings for multiple patients and can be used to adjust the stimulation parameters outside of the operations room. It is capable of changing the stimulation parameters though the RF wireless dongle 200 when the trial generator 107 or IPG 102 which has been implanted in the patient is within the RF range. In addition, it is also capable of setting or changing the stimulation parameters on the trial generator 107 and/or the IPG 102 through the internet when both the tablet 204 and the Patient Programmers on a smartphone/mobile device 202 both have access to the internet.

The Patient Programmer is an application that is installed on a smartphone/mobile device 202. It is used by the patient to set the stimulation parameters on the trial generator 107 or IPG 102 after trial and permanent implantation outside the operating room. The clinician programmer is capable of saving multiple settings for multiple patients and can be transferred to the Patient Programmer wirelessly when the Clinician Programmer tablet 204 and the Patient Programmer smartphone/mobile device 202 are within wireless range such as Bluetooth from each other. In the scenario where the Clinician Programmer tablet 204 and the Patient Programmer smartphone/mobile device 202 are out of wireless range from each other, the data can be transferred through the internet where both devices 202, 204 have wireless access such as Wi-Fi. The Patient Programmer is capable of changing the stimulation parameters on the trial generator 107 or IPG 102 though the RF wireless dongle 200 when the trial generator 107 or IPG implanted in the patient is within the RF range.

Tuohy Needle

Figure 15:
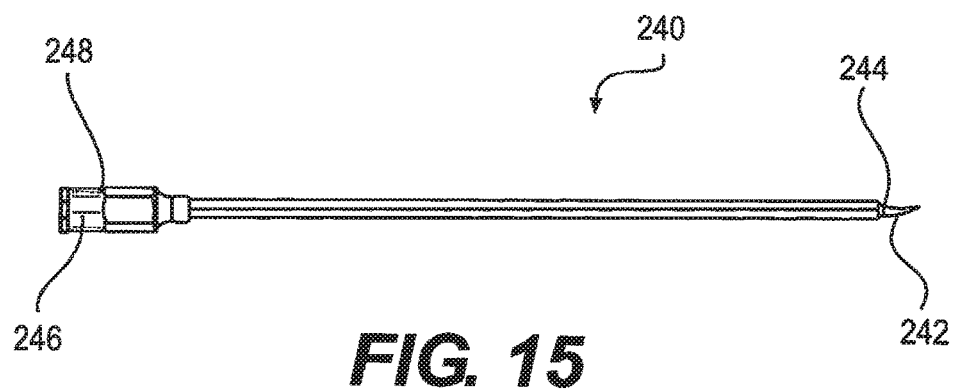
FIG. 15 depicts a Tuohy needle, according to an embodiment.

The Tuohy needle 240, as depicted in FIG. 15, is used in conjunction with a saline-loaded syringe for loss-of-resistance needle placement, and percutaneous stimulation leads 140, for lead 140 placement into the spinal canal. The Tuohy epidural needle 240 is inserted slowly into the spinal canal using a loss-of-resistance technique to gauge needle 240 depth. Once inserted to the appropriate depth, the percutaneous stimulation lead 140 is passed through the needle 240 and into the spinal canal.

The epidural needle 240 is a non-coring 14G stainless steel spinal needle 240 and will be available in lengths of 5" (127 mm) and 6" (152.4). The distal tip 242 of the needle 240 has a slight curve to direct the stimulation lead 140 into the spinal canal. The proximal end 246 is a standard Leur-Lock connection 248.

Stylet

Figure 16:
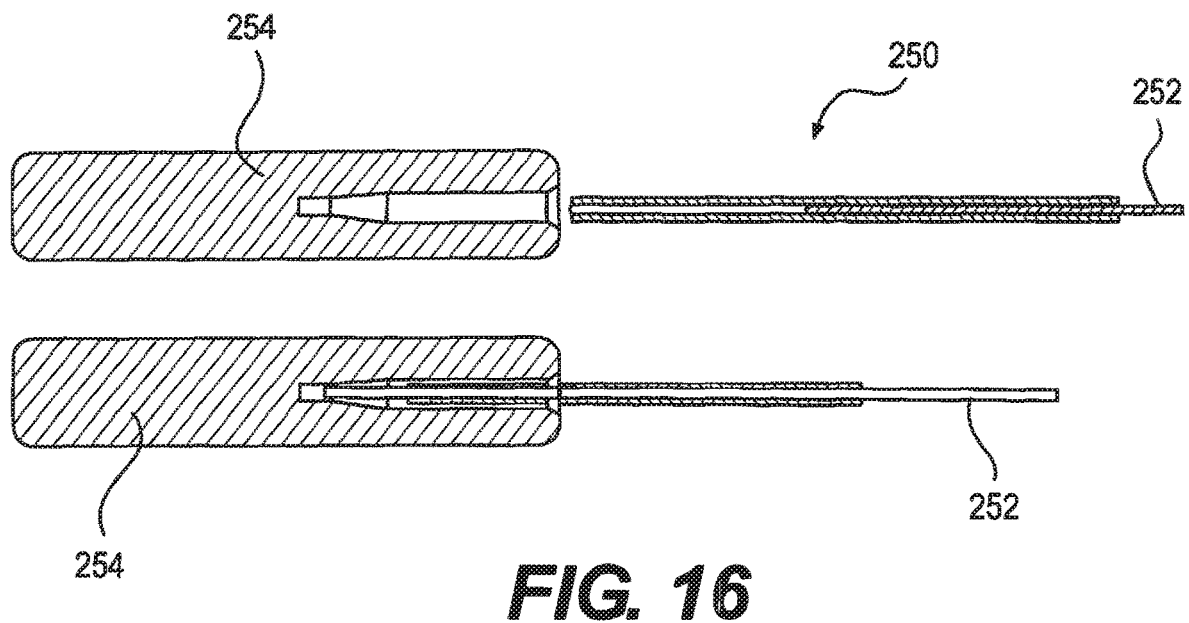
FIG. 16 depicts a stylet, according to an embodiment.

The stylet 250, as depicted in FIG. 16, is used to drive the tip of a percutaneous stimulation lead 140 to the desired stimulation zone by adding rigidity and steerability. The stylet 250 wire 252 passes through the center lumen 142 of the percutaneous lead 140 and stops at the blocking plug at the distal tip of the lead 140. The tip of the stylet 250 comes with both straight and curved tips. A small handle 254 is used at the proximal end of the stylet 250 to rotate the stylet 250 within the center lumen 142 to assist with driving. This handle 254 can be removed and reattached allowing anchors 170 to pass over the lead 140 while the stylet 250 is still in place. The stylet 250 wire 252 is a PTFE coated stainless steel wire and the handle 254 is plastic.

Passing Elevator

Figure 17:
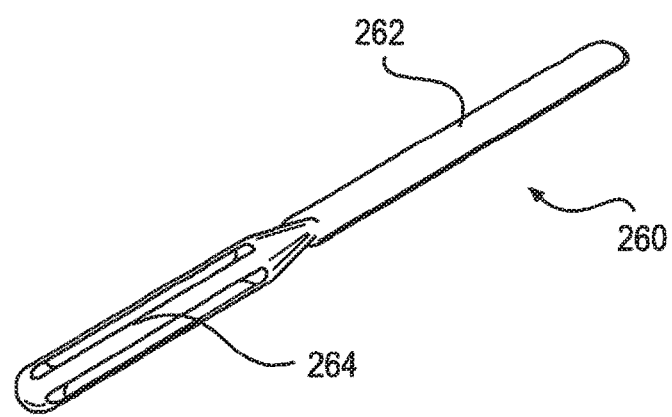
FIG. 17 depicts a passing elevator, according to an embodiment.

The passing elevator 260, as depicted in FIG. 17, is used prior to paddle lead 141 placement to clear out tissue in the spinal canal and help the surgeon size the lead to the anatomy. The passing elevator 260 provides a flexible paddle-shaped tip 262 to clear the spinal canal of obstructions. The flexible tip is attached to a surgical handle 264.

The passing elevator 260 is a one-piece disposable plastic instrument made of a flexible high strength material with high lubricity. The flexibility allows the instrument to easily conform to the angle of the spinal canal and the lubricity allows the instrument to easily pass through tissue.

Tunneling Tool

Figure 18:
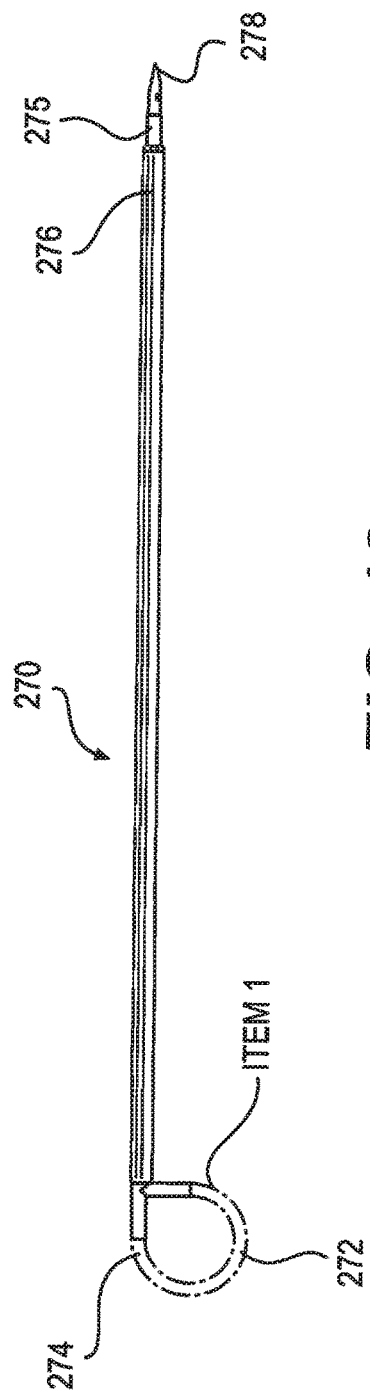
FIG. 18 depicts a tunneling tool, according to an embodiment.

The tunneling tool 270, as depicted in FIG. 18, is used to provide a subcutaneous canal to pass stimulation leads 140 from the entrance point into the spinal canal to the IPG implantation site. The tunneling tool 270 is a long skewer-shaped tool with a ringlet handle 272 at the proximal end 274. The tool 270 is covered by a plastic sheath 276 with a tapered tip 278 which allows the tool 270 to easily pass through tissue. Once the IPG 102 implantation zone is bridge to the lead 140 entrance point into the spinal canal, the inner core 275 is removed, leaving the sheath 276 behind. The leads 140 can then be passed through the sheath 276 to the IPG 102 implantation site. The tunneling tool 270 is often bent to assist in steering through the tissue.

The tunneling tool 270 is made of a 304 stainless steel core with a fluorinated ethylene propylene (FEP) sheath 276. The 304 stainless steel is used for its strength and ductility during bending, and the sheath 276 is used for its strength and lubricity.

Torque Wrench

Figure 19:
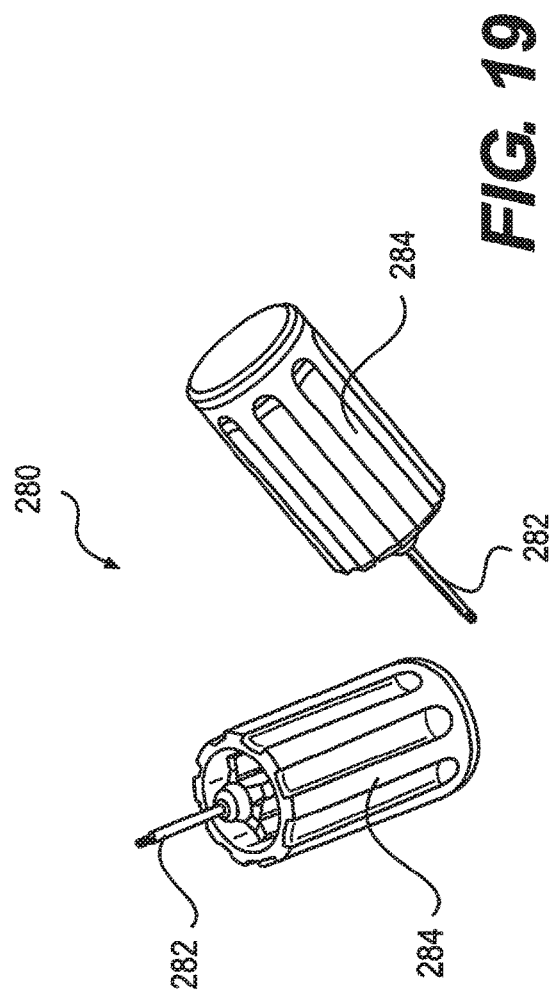
FIG. 19 depicts a torque wrench, according to an embodiment.

The torque wrench 280, as depicted in FIG. 19, is used in conjunction with the IPG 102, lead extension 150 and lead splitter 160 to tighten the internal set screw 119, which provides a radial force against the fixation contact of the stimulation leads 140, 141, preventing the leads 140, 141 from detaching. The torque wrench 280 is also used to lock and unlock the anchor 170. The torque wrench 280 is a small, disposable, medical instrument that is used in every SCS 100 case. The torque wrench 280 provides audible and tactile feedback to the surgeon that the lead 140, 141 is secured to the IPG 102, extension 150, or splitter 160, or that the anchor 170 is in the locked or unlocked position.

The torque wrench 280 is a 0.9 mm stainless steel hex shaft 282 assembled with a plastic body 284. The wrench's 280 torque rating is bi-directional, primarily to provide feedback that the anchor 170 is either locked or unlocked. The torque rating allows firm fixation of the set screws 119, 152 against the stimulation leads 140, 141 without over-tightening.

Trial Patch

The trial patch is used in conjunction with the trialing pulse generator 107 to provide a clean, ergonomic protective cover of the stimulation lead 140, 141 entrance point in the spinal canal. The patch is also intended to cover and contain the trial generator 107. The patch is a large, adhesive bandage that is applied to the patient post-operatively during the trialing stage. The patch completely covers the leads 140, 141 and generator 107, and fixates to the patient with anti-microbial adhesive.

The patch is a watertight, 150 mm×250 mm anti-microbial adhesive patch. The watertight patch allows patients to shower during the trialing period, and the anti-microbial adhesive decreases the risk of infection. The patch will be made of polyethylene, silicone, urethane, acrylate, and rayon.

Magnetic Switch

The magnetic switch is a magnet the size of a coin that, when placed near the IPG 102, can switch it on or off. The direction the magnet is facing the IPG 102 determines if the magnetic switch is switching the IPG 102 on or off.

Figure 20:
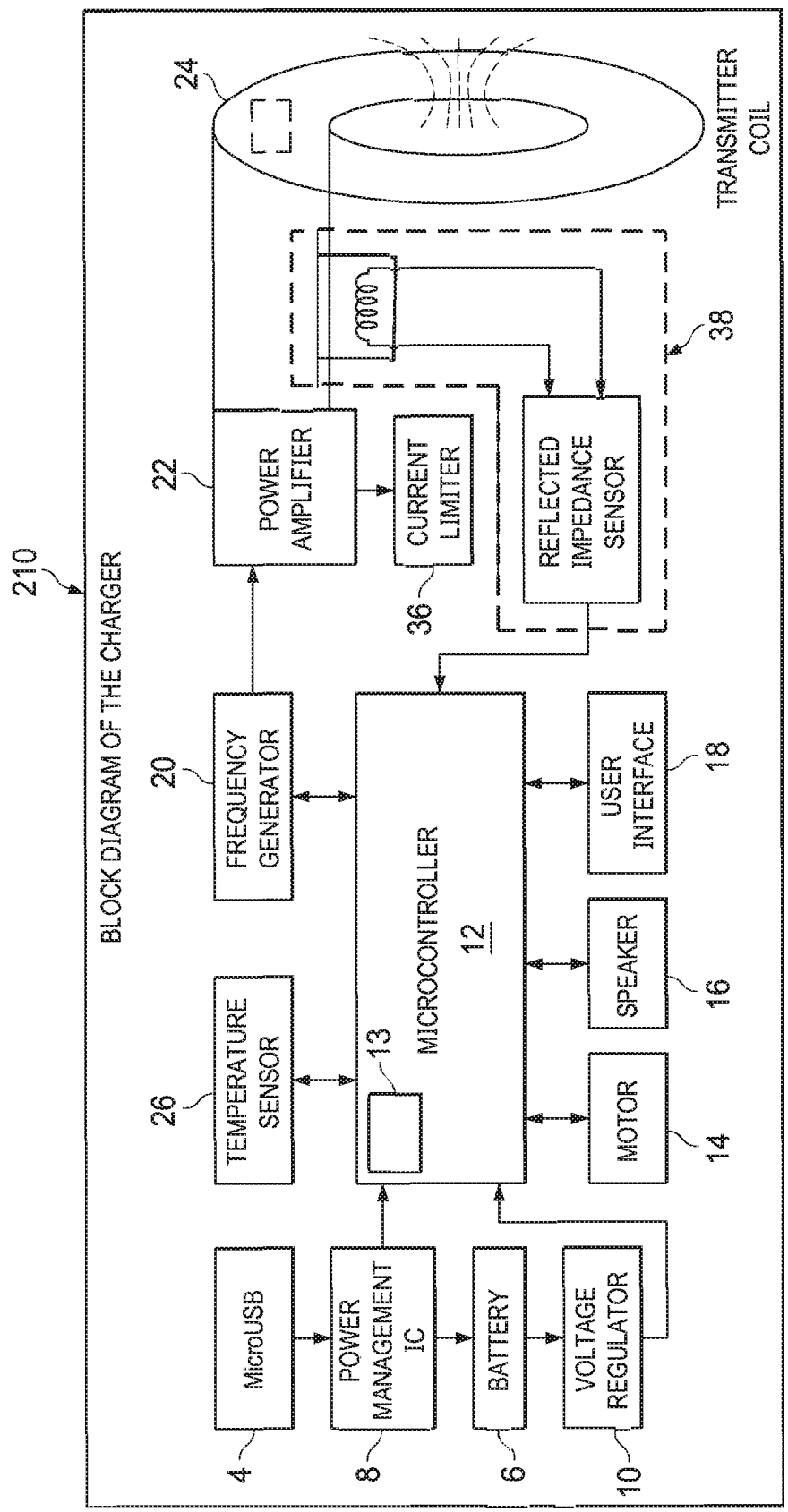
FIG. 20 is a function block diagram of a wireless charger according to an embodiment.

FIG. 20 is a functional block diagram of a wireless charger 210 according to the present invention. As discussed above, the wireless charger 210 has a micro usb port 4 which is connectable to an external power supply (not shown) to receive DC power for charging the lithium ion rechargeable battery 6. In the embodiment shown, the rechargeable battery 6 is a 4.2V battery. A power management circuit 8 regulates the power from the port 4 to proper voltage and current which is used to charge the battery 6.

A processor 12 such as a microcontroller controls the charging process and is powered by the battery 6. Since the processor 12 uses 3.3V, a voltage regulator 10 connected to the battery 6 regulates the battery voltage down to 3.3V for powering the processor.

A vibrator such as a vibration motor 14 for producing a vibrating tactile feedback as well as a buzzer/speaker 16 for creating sound feedback for the user are connected to and are controlled by the processor 12. The vibrator 12 is similar to those used for cellular telephones, game controllers, tablets and the like. For example, a vibration motor part number 28821 from Parallex Inc. of Rocklin, Calif. can be used.

A user interface 18 is connected to the processor 12 to interact with the charger 210. The user interface 18 may include buttons and switches for turning the charger 210 on and off and for changing the volume of the sound and motor from the vibrator 14 and speaker 16.

A frequency generator 20 coupled to the processor 12 generates a high frequency signal under the control of the processor. For example, in one embodiment, the processor 12 controls the frequency generator 20 to generate a high frequency charging signal of between 80 kHz and 90 kHz. A power amplifier 22 coupled to the frequency generator 20 generates an amplified charging signal under the control of the charging signal. The amplifier 22 then feeds the amplified charging signal to a charging coil 24, which is placed on one side of a printed circuit board (PCB). In one embodiment, the amplified charging signal is a sine wave signal having a peak to peak voltage of 500V. The charging coil 24 generates a magnetic field for inducing power into the IPG 102 as will be discussed in more detail herein.

Figure 21:
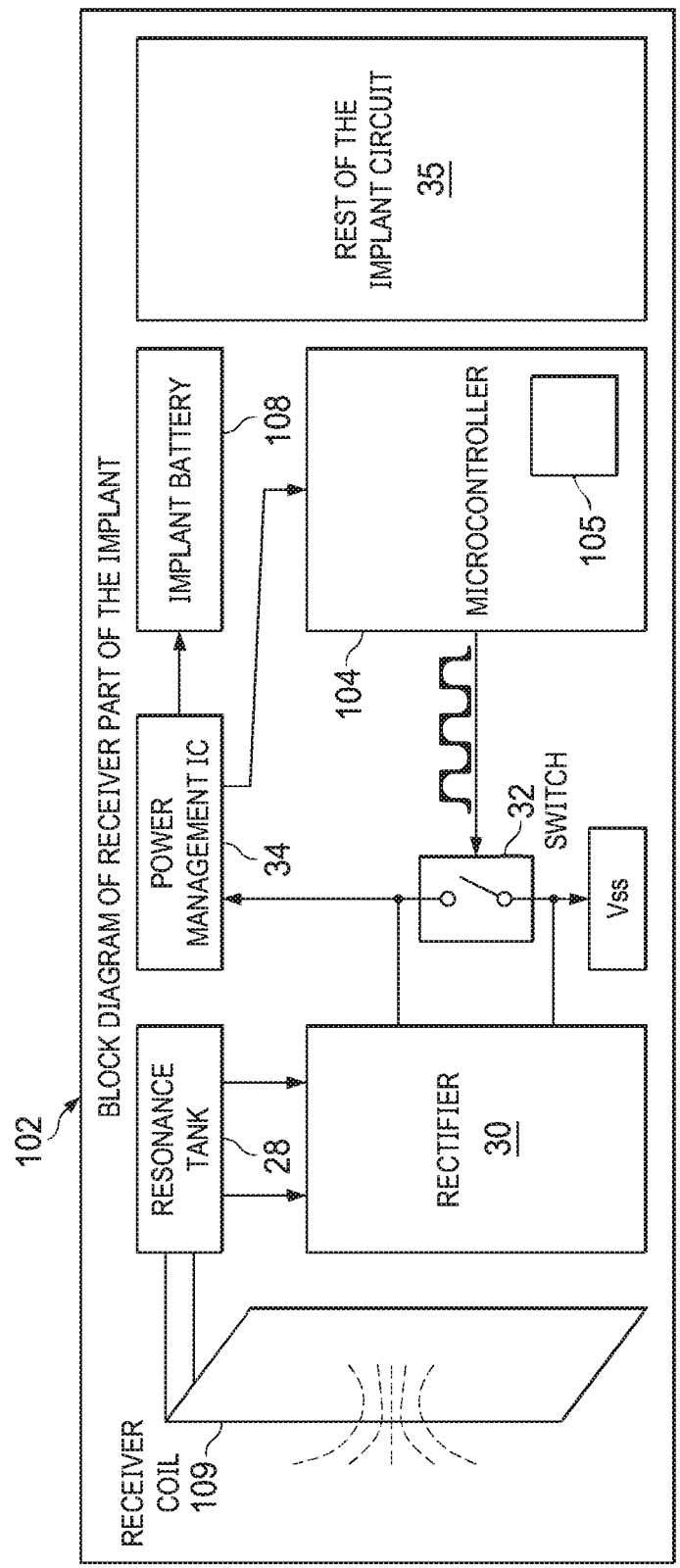
FIG. 21 is a function block diagram of an implantable pulse generator according to an embodiment.

In the IPG 102 as partially shown in FIG. 21, the receiving coil 109 is inductively and wirelessly coupled to the charging coil 24 when they are positioned near each other. The magnetic field from the charging coil 24 induces voltage in the receiving coil 109. As an example, the induced voltage is an oscillating voltage with a swing of +3V to −3V for a peak to peak voltage of 6V. A resonance tank 28 which includes a capacitor connected in series with the receiving coil 109 comprises a resonance circuit whose resonance frequency is tuned to the frequency of the magnetic field emanating from the charging coil 24. The induced voltage is rectified by a rectifier 30 to convert an oscillating voltage into a DC voltage. In the embodiment shown, the rectifier 30 is a full wave voltage doubler rectifier so as to generate a 6V DC at its output. The IPG processor 104 such as a microcontroller controls a switch 32 connected across the rectifier 30 in parallel. One end of the switch 32 is connected to a power management circuit 34 while the other end is connected to ground Vss. In one embodiment, the switch 32 is a MOSFET transistor that can be turned on or off by the processor 104. Normally, the switch 32 is turned off including the time when the battery 108 is being charged.

The power management circuit 34 receives the rectified DC voltage from the rectifier 30 and charges the rechargeable battery 108. Other circuits 35 control the actual generation and controlling of the spinal cord stimulation signals.

Figure 22:
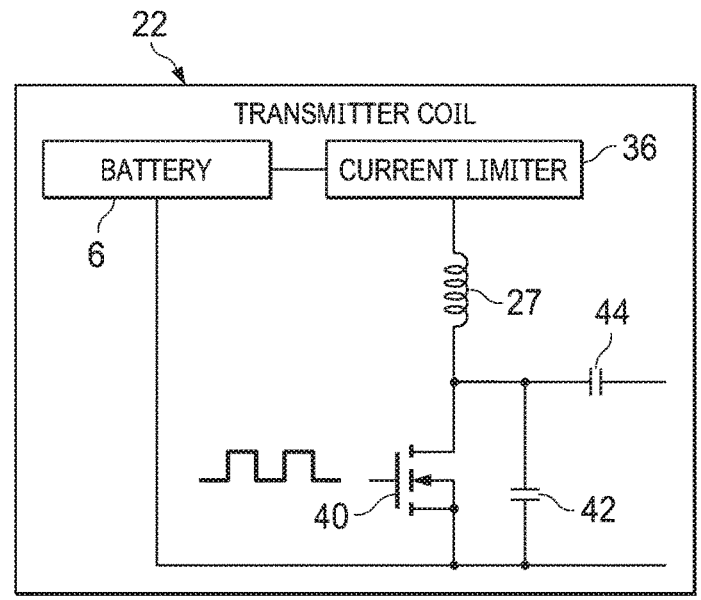
FIG. 22 is a functional block diagram of a Class-E amplifier of the wireless charger according to an embodiment.

In one embodiment, the amplifier 22 is a class-E amplifier as shown in FIG. 22. The amplifier 22 includes a switch 40 receiving the charging signal from the frequency generator 20, LC circuit including capacitors 42,44 and a choke 37 connected to the voltage source 6. The choke 37 in the embodiment shown is an inductor that helps to smooth the power supply to the power amplifier circuit. The switch 40 as shown is an N-channel MOSFET which is controlled by the frequency generator 20. In some operating conditions for this type of amplifier, it is possible that the switch 40 can connect the voltage source directly to ground, effectively creating an electrical short, however fleeting it may be. That creates at least two issues. First, there will be a rapid drain of high current from source to ground which is a waste of power. Second, the short drops the source voltage significantly to cause a malfunction in other parts of the charger 210. This may cause some circuits to behave erratically which is highly undesirable.

One solution is to use a current limiting resistor in the current path of the amplifier 22. Although that solution reduces the maximum drain current, it also reduces the current that goes into the charging coil 24. A preferred solution is to use a current limiter 36 connected between the power source 6 and the RF choke 37 of the amplifier 22 to limit the current being provided to the threshold value. In one embodiment, the current limiter 36 is an integrated circuit chip NCP380LSNAJAAT1G from ON Semiconductor of Phoenix, Ariz. In the embodiment shown, the current limiter 36 has been programmed to limit the current to a maximum threshold current of 0.5 Amps. In the case of a short circuit between the voltage source 6 and ground through the MOSFET switch 40, the current limiter 36 will not allow the amplifier 22 to drain more than the maximum current set limit of 0.5 Amps, for example. The current limiter 36 also avoids a significant voltage drop of the voltage source, thereby allowing the rest of the electronic circuits to function normally.

The wireless charger 210 produces a high frequency, high voltage magnetic field. The charging coil 24 has a resistance and the resistive losses will be dissipated in the form of heat. Heat raises the temperature of the charger 210. When the temperature of the charger 210 rises significantly, the charger might cause minor discomfort in most of the cases and minor tissue burns in some rare cases.

According to Standards IEC60101-1, temperature of the surface of a device that is in physical contact with a patient's body shall be limited to 41 C. To control the heat, a temperature sensor 26 is used to monitor the temperature of the charger 210. The charging coil 24 is a flat round shaped coil on one side of the PCB. In one embodiment, a ferrite plate can be disposed between the coil and the PCB. On the other side of the PCB, the temperature sensor 26 such as a thermistor 26 is placed behind the coil 24 and is coupled to the processor 12. In one embodiment, the coil 24 has an inner diameter of about 25 mm and an outer diameter of about 60 mm. In one embodiment, the temperature sensor 26 is placed in the middle of the coil at about 42.5 mm from the coil center between the inner winding and outer winding. In this way, the highest temperature of the coil 24 can generally be measured.

The processor 12 is programmed to monitor the temperature from the temperature sensor 26 regularly and when the monitored temperature rises above a first threshold value, the processor turns off the frequency generator 20 and power amplifier 22. The processor 12 continues to monitor the temperature from the temperature sensor 26 and will turn the frequency generator 20 and power amplifier 22 back on automatically when the monitored temperature falls below a second threshold value. Thus, there is a hysteresis band between the high and low thresholds to avoid the charger 210 from rapidly switching on and off near the set temperature limit. Turning off the charging function when necessary will reduce patient's discomfort and likely avoid any tissue burns. One example of first and second threshold temperatures may be 40 C and 38 C, respectively.

According to another aspect of the present invention, a charger alignment feature for more efficiently transferring power into the IPG 102 will now be explained. A charge alignment software is stored in an internal memory 13 of the microcontroller 12 and is executed when the charger 210 is turned on. For this feature, a reflected impedance sensor 38 is used to measure a reflected impedance to detect a reflected impedance of the charging coil 24. Thus, a charge alignment circuit comprises the stored charge alignment software, processor 12 and reflected impedance sensor 38.

Figure 23:
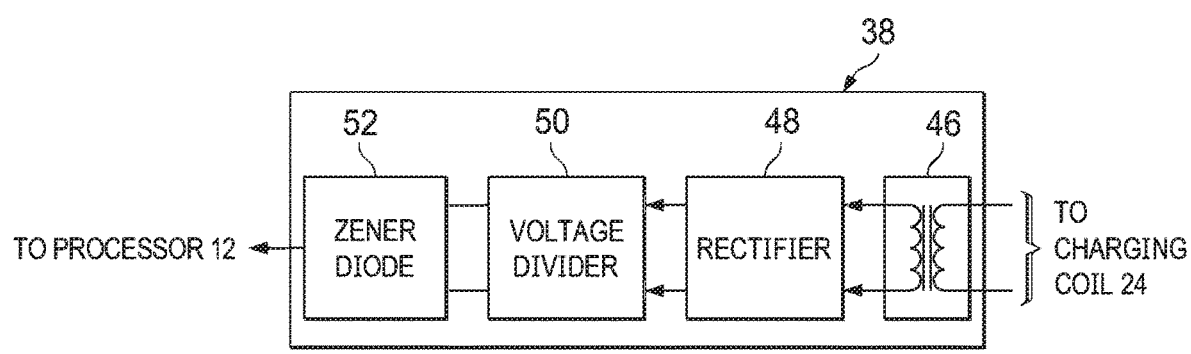
FIG. 23 is a functional block diagram of a reflected impedance sensor of the wireless charger according to an embodiment.

As shown in FIG. 23, the sensor 38 includes a small transformer 46 having a primary coil connected to the charging coil 24 in series to detect the current flowing through the charging coil. The secondary coil of the transformer 46 is electromagnetically coupled to the primary coil. The primary coil acts as a sensor to sense the voltage across the charging coil. The sensor 38 also includes a rectifier 48 (e.g., half wave rectifier in the embodiment shown) to rectify AC current from the secondary coil of the transformer 46 into DC. In the embodiment shown, the DC voltage can swing between zero and about 5 Volt. The rectified voltage represents a voltage level of the charging coil 24. A one-to-one voltage divider 50 divides the DC voltage to make the DC voltage compatible with the operating voltage (e.g., 3.3 Volt) of the microcontroller 12. Zener diode 52 connected between the voltage divider 50 and ground ensures that the voltage from the voltage divider 50 does not rise above the operating voltage of the processor 12 by sinking current to ground if it does.

The output of the reflected impedance sensor 38 is connected to the processor 12. Typically, when the IPG 102 is far away and not receiving any current from the charger 210, the output voltage of the sensor 38 is around 2.3-2.4 Volt. On the other hand, when the charging coil 24 of the charger 210 is perfectly aligned with the receiving coil 109 of the IPG 102, i.e., the charging coil is directly above the receiving coil 109, the output voltage of the sensor 38 drops to around 1.6 -1.7 Volt. A threshold voltage value of around 1.8 Volt is set such that any output voltage of the reflected impedance sensor 38 below that threshold voltage value is considered to be aligned for maximum charging current transfer from the charger 210 to the IPG 102.

Under the control of the charge alignment software, the microcontroller 12 continuously monitors and compares the output of the reflected impedance detected by the sensor 38 against the threshold value and controls the vibrator 14 and speaker 16 to provide audible and tactile feedback to the user/patient based on the detected reflected impedance values. Thus, the outputs of the vibrator 14 and speaker 16 are indicative of the alignment of the charging coil 24 to the receiving coil 109.

In one embodiment, as the sensor 38 output decreases towards the threshold value, meaning that the charging coil 24 is becoming more aligned with the receiving coil 109, the processor 12 controls the vibrator 14 to vibrate at a lower rate. When the sensor 38 output reaches and goes past the threshold value, the processor 12 stops the vibrator 14 from vibrating. For example, the initial vibrator frequency can be 8-9 Hertz, vibrating for 0.1 second each time. As the charger 210 comes closer to the IPG 102, the vibrating frequency can correspondingly decrease to 1-2 Hertz with the same 0.1 second vibrating duration. When the charger 210 is fully aligned, i.e., the output of the sensor 38 has reached the threshold value, then the processor 12 stops the vibrator 14 from vibrating to indicate that the charger 210 is now fully aligned with the IPG 102. Thus, in this embodiment, although the vibration rate decreases, vibration is continuous until the charging coil 24 is fully aligned with the receiving coil 109.

At the same time, the processor 12 controls the speaker 16 to generate a tone (e.g., beeps) having the same frequency and duration as the vibrator 14. In other words, the processor 12 can control the speaker 16 to make a tone at the initial interval of 8-9 Hertz, generating the sound for 0.1 second each time. As the charger 210 comes closer to the IPG 102, the tone can correspondingly decrease to 1-2 Hertz with the same 0.1 second sound duration. When the charger 210 is fully aligned, i.e., the output of the sensor 38 has reached the threshold value, then the processor 12 stops the speaker 16 from generating any sound to indicate that the charger 210 is now fully aligned with the IPG 102.

In another embodiment, as the sensor 38 output decreases towards the threshold value, the processor 12 controls the vibrator 14 to vibrate at a higher rate. When the sensor 38 output reaches the threshold value, the processor 12 controls the vibrator 14 to vibrate constantly. For example, the initial vibrator frequency can be 1 Hertz, vibrating for 0.1second each time. As the charger 210 comes closer to the IPG 102, the vibrating frequency can correspondingly increase to 8-9 Hertz with the same 0.1 second vibrating duration. When the charger 210 is fully aligned, i.e., the output of the sensor 38 has reached the threshold value, then the vibration can be constant. Thus, in this embodiment, although the vibration rate increases, vibration is continuous until the charging coil 24 is fully aligned with the receiving coil 109 at which point the vibration becomes constant. Once the alignment has been accomplished and after a certain time period has elapsed, e.g., 30 seconds, the processor 12 controls the vibrator 14 to stop the constant vibration.

At the same time, the processor 12 controls the speaker 16 to generate a tone (e.g., beeps) having the same frequency and duration as the vibrator 14. In other words, the processor 12 can control the speaker 16 to make a tone at the initial interval of 1-2 Hertz, generating the sound for 0.1 second each time. As the charger 210 comes closer to the IPG 102, the tone can correspondingly increase to 8-9 Hertz with the same 0.1 second sound duration. When the charger 210 is fully aligned, i.e., the output of the sensor 38 has reached the threshold value, then the processor 12 controls the speaker 16 to generate a continuous tone to indicate that the charger 210 is now fully aligned with the IPG 102. Once the alignment has been accomplished and after a certain time period has elapsed, e.g., 30 seconds, the processor 12 controls the speaker 16 to stop the continuous tone.

As can be appreciated, the vibrator 14 providing tactile feedback to the patient can be very important because in certain environments, the patient may not be able to hear the audible feedback from the speaker 16.

In the IPG 102, the receiving coil 109 is inductively coupled to the charging coil 24 when they are positioned near each other. The magnetic field from the charging coil 24 induces voltage in the receiving coil 109. As an example, the induced voltage is an oscillating voltage with a swing of +3V to -3V for a peak to peak voltage of 6V. A resonance tank 28 which includes a capacitor connected in series with the receiving coil 109 comprises a resonance circuit whose resonance frequency is tuned to the frequency of the magnetic field emanating from the charging coil 24. The induced voltage is rectified by a rectifier 30 to convert an oscillating voltage into a DC voltage. In the embodiment shown, the rectifier 30 is a full wave voltage doubler rectifier so as to generate a 6V DC at its output. The IPG processor 104 such as a microcontroller controls a switch 32 connected across the rectifier 30 in parallel. One end of the switch 32 is connected to a power management circuit 34 while the other end is connected to ground Vss. In one embodiment, the switch 32 is a MOSFET transistor that can be turned on or off by the processor 104. Normally, the switch 32 is turned off including the time when the battery 108 is being charged.

The power management circuit 34 receives the rectified DC voltage from the rectifier 30 and charges the rechargeable battery 108. Other circuits 35 control the actual generation and controlling of the spinal cord stimulation signals.

Once the charger 210 and the implanted IPG 102 are aligned, the charger is strapped to the body of the patient so that it is fixed relative to the IPG and the charger starts charging the IPG battery 108. However, when the charger 210 continues to charge the battery 108 in the IPG 102 even when it has fully charged, the extra induced power can potentially damage the various circuits in the IPG. To prevent such damage, the charger 210 would need to turn off the power amplifier 22. Since there is no active communication from the IPG 102 to the charger 210, it is a challenge to detect when the battery 108 of the IPG 102 has fully charged.

According to another aspect of the present invention, a novel way of detecting the end-of-charge is disclosed. When the power management circuit 34 determines that the IPG battery 108 has been fully charged, it sends an end-of-charge signal to the IPG processor 104. A small end-of-charge software is stored in an internal memory 105 of the processor 104 and is executed by the processor upon receiving the end-of-charge signal from the power management circuit 34. Under the control of the stored end-of-charge software, the processor 104 turns on and off the switch 32 to electrically short the receiving coil 109 to ground in a selected pattern.

For example, the switch 32 could be turned on and off at 1 Hertz for at least 3-5 times with a 50% duty cycle. In other words, the switch 32 could be on for 0.5 second and off for 0.5 second, and the on-off operation of the switch could be repeated at least 3 times, preferably at least 5 times and most preferably at least 10 times.

At the charger 210, a small end-of-charge detection software is stored in the internal memory of the processor 12 and is executed by the processor. The end-of-charge detection software continuously monitors the reflected impedance values from the sensor 38 for purposes of detecting an end-of-charge signal from the IPG 102. The processor 12 and the internally stored end-of-charge detection software comprise an end-of-charge detection circuit. When the switch 32 from the IPG 102 turns on and off repeatedly, the electrical short created by the switch causes the output of the sensor 38 to go up and down in a predetermined pattern according to the on-off switching pattern of the IPG switch. In one embodiment, the predetermined pattern is a sine wave shape. The processor 12 could detect the end-of-charge by recognizing that pattern. For example, if the on-off state of the switch 32 is repeated 10 times, then the processor 12 could count the number of times the sensor 38 output rises above a threshold value. If the number is 8 or greater, then the processor could determine that the end-of- charge status of the battery 108 has been reached.

Alternatively, the processor 104 could vary the current being received by the receiving coil 109 in a selected pattern which corresponds to the predetermined pattern of the reflected impedance sensed by the sensor 38. This could be accomplished, for example, by varying the amount of on or off state of the switch 32.

Once the processor 12 determines that the end-of-charge status has been reached, it controls the vibrator 14 and the speaker 16 to output tactile and audible signals which is indicative of the end-of-charge status of the IPG battery 108. For example, the vibration and beep could last for 0.1 second, two times a second for about 10 seconds. Thereafter, the processor 12 could turn off the current to the charging coil 24 and possibly turn itself off completely.

The charging frequency of the power amplifier 22 is at a set frequency which ensures maximum power transfer to the IPG 102. In the embodiment shown, the charging frequency is set at about 85 kHz which is the optimum resonant frequency of the charger 210 and IPG 102 at an ideal separation distance of 15 mm.

However, the optimum operating frequency may change from the 85 kHz set frequency depending on many factors such as the presence of metallic objects near the charger 210, proximity and size of such objects and the like. Presence of metallic objects can affect the optimum operating frequency by as much as a few kHz in either direction. Consequently, operating the charger at only one set frequency may limit the maximum achievable power transfer to the IPG 102.

According to another aspect of the present invention, a novel way of optimizing the charging frequency is disclosed. An optimization circuit selects an optimum frequency of a charging signal supplied to the charging coil 24 based on evaluation of the reflected impedances of a group of charging frequencies in a selected frequency range. An optimization software is stored in the internal memory 13 of the processor 12 and is programmed to be executed by the processor at set time intervals. For example, the optimization software is programmed to be executed about every half a minute to about 5 minutes.

The optimization software, processor 12 and reflected impedance sensor 38 comprise the optimization circuit. In short, the optimization circuit sweeps the charging frequencies within a small band of frequencies with a selected step size. At every frequency step, the charger 210 estimates the power transfer and moves to the next frequency step. At the end of sweeping the frequency band, the charger will be set to the frequency at which the estimated power transfer is the highest. The sweeping of the frequencies to find the optimum operating frequency by the optimization software will be performed once in about 30 seconds to about 5 minutes to ensure optimum operation. At each frequency step, the power transfer is estimated based on the peak to peak voltage in the magnetic coil 24 as measured by the reflected impedance sensor 38.

Figure 24:
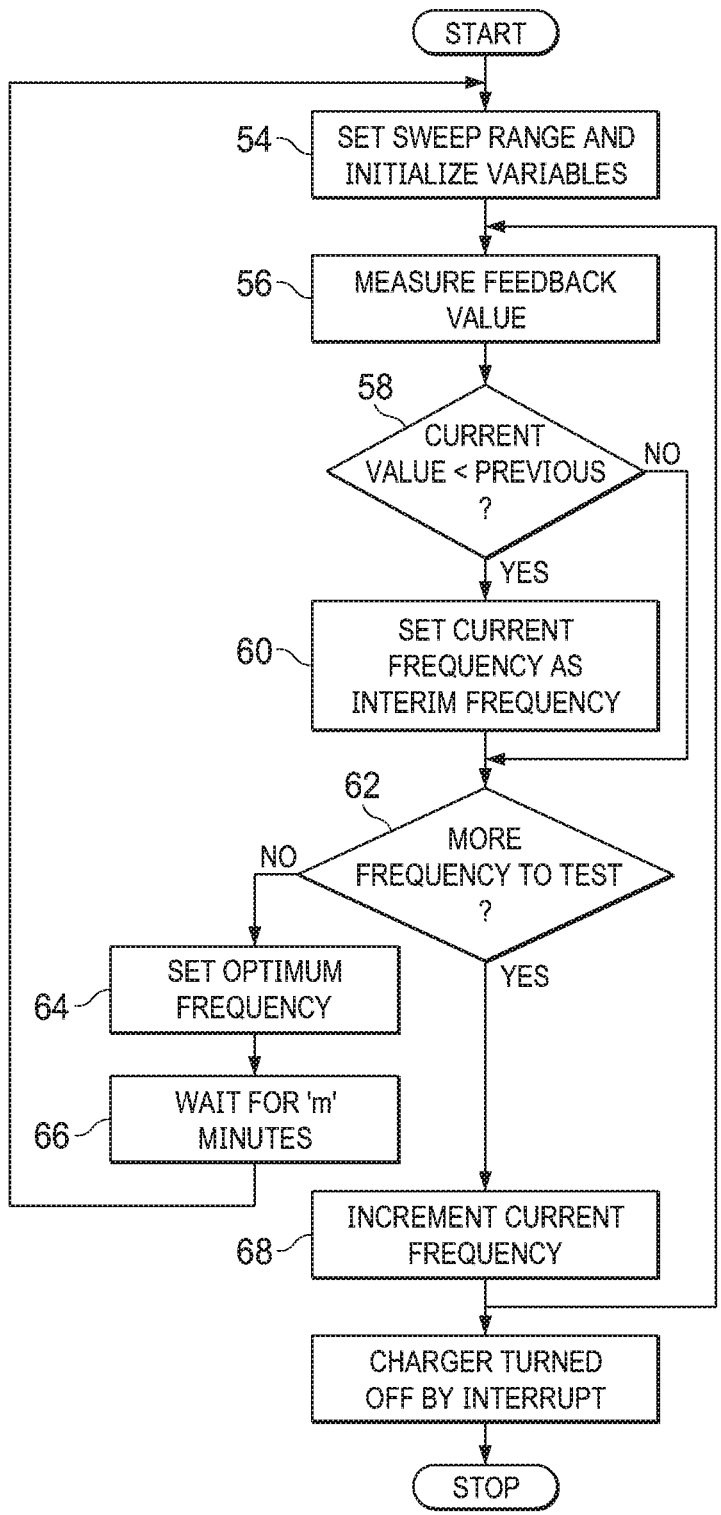
FIG. 24 is a flowchart for a method of optimizing the charging frequency of the wireless charger according to an embodiment.

FIG. 24 is a detailed flowchart of the steps to optimizing the charging frequency by the optimization software. In step 54, the software sets a sweep frequency range and initializes various variables. The selected sweep frequency range in one embodiment is 80 kHz to 90 kHz. In step 54, an initial frequency is set to the lowest frequency in the range, and the selected step interval is set at 100 Hz. Thus, sweeping across the 80-90 kHz range takes 100 iterations.

In step 56, the reflected impedance sensor 38 continuously detects a reflected impedance of the charging coil 24 and the optimization circuit receives the detected reflected impedance values from the sensor. The processor 12 under the control of the optimization software receives at least several values from the sensor 38 and averages them. In one embodiment, the processor stores 10 values from the sensor 38 sequentially and then averages them to produce a current average reflected impedance value.

In step 58, the processor 12 determines whether the current average value is lower than the interim stored value which represents the lowest reflected impedance value during the sweep. If so, that means that at the current frequency being evaluated, less current is being detected by the sensor 38 as more current/power is being transferred to the IPG 102. Control then transfers to step 60 where the current frequency is set to the interim optimal frequency. On the other hand, if the processor 12 determines that the current average value is higher than the interim stored value, then at the frequency being evaluated, less current/power is being transferred to the IPG 102 and control passes to step 62.

At step 62, the processor 12 determines whether there is any more frequency to evaluate. If so, control passes to step 68. At step 68, the current frequency is incremented by the selected step interval (e.g., 100 Hz) and the evaluation process of steps 54-68 are repeated for the next frequency.

However, if the processor 12 determines that there are no more frequencies to evaluate, control passes to step 64 where the optimum frequency of the charging signal to the charging coil 24 is set to the interim optimal frequency which corresponds to the lowest interim stored value. In step 66, once the optimal frequency has been set, the optimization circuit waits for 'm' minutes and the entire evaluation process repeats starting from step 54. In one embodiment, "m" is between 0.5 minute and 5 minutes. For example, "m" could be set to 2 minutes.

The entire frequency sweep from 80 kHz to 90 kHz can be done in less than 15 seconds, and preferably in less than 10 seconds.

The foregoing specific embodiments represent just some of the ways of practicing the present invention. Many other embodiments are possible within the spirit of the invention. Accordingly, the scope of the invention is not limited to the foregoing specification, but instead is given by the appended claims along with their full range of equivalents.

What is claimed is:

1. A method, comprising:
  receiving, by a charger during a charging of an implantable medical device, a signal from the implantable medical device, wherein the signal causes a sensor of the charger to produce an output;
  comparing, by the charger, a pattern of the output produced by the sensor with a predefined pattern;
  determining, by the charger and based on the comparing, that the implantable medical device no longer needs to be charged; and
  performing, by the charger, an action in response to the determining.

2. The method of claim 1, wherein the performing the action comprises communicating, to a user of the charger, a tactile feedback signal or an audible feedback signal via the charger.

3. The method of claim 1, wherein the performing the action comprises terminating the charging of the implantable medical device.

4. The method of claim 1, wherein the signal causes the output of the sensor of the charger to go up and down.

5. The method of claim 1, wherein the predefined pattern comprises a sine wave.

6. The method of claim 1, wherein the determining comprises:
  counting a number of times the output produced by the sensor rises above a threshold value; and
  determining that the implantable medical device no longer needs to be charged when the counted number of times exceeds a predetermined number.

7. The method of claim 1, wherein the charging of the implantable medical device is performed via a charging coil of the charger, and wherein the method further comprises:
  sensing an electrical current flowing through the charging coil or a voltage across the charging coil via a transformer of the sensor.

8. The method of claim 1, wherein the implantable medical device is charged via a receiving coil of the implantable medical device, and wherein the method further comprises:
  determining, by the implantable medical device, that a rechargeable battery of the implantable medical device has been sufficiently charged; and
  in response to the determining that the rechargeable battery has been sufficiently charged, electrically shorting the receiving coil to ground repeatedly, thereby producing the signal.

9. A system, comprising:
a charging coil configured to charge a rechargeable battery of an implantable medical device;
a sensor circuit coupled to the charging coil, wherein the sensor circuit is configured to detect an electrical current flowing through the charging coil or a voltage across the charging coil; and
a controller coupled to the sensor circuit and to the charging coil, wherein the controller is configured to:
compare an output of the sensor circuit with a predefined pattern; and
determine, based on a match between the output of the sensor circuit and the predefined pattern, that the rechargeable battery no longer needs to be charged.

10. The system of claim 9, wherein the controller is further configured to play a tactile feedback signal or an audible feedback signal in response to a determination that the rechargeable battery no longer needs to be charged.

11. The system of claim 9, wherein the controller is further configured to terminate a charging of the rechargeable battery in response to a determination that the rechargeable battery no longer needs to be charged.

12. The system of claim 9, wherein the predefined pattern comprises a pattern that goes up and down.

13. The system of claim 12, wherein the predefined pattern comprises a sine wave.

14. The system of claim 9, wherein:
the controller counts a number of times the output produced by the sensor circuit rises above a threshold value; and
the controller determines that the rechargeable battery no longer needs to be charged only when the number of times exceeds a predetermined number.

15. The system of claim 9, wherein: the sensor circuit comprises a transformer that includes a primary coil and a secondary coil that is electromagnetically coupled to the primary coil; and
the primary coil is coupled to the charging coil in series.

16. The system of claim 15, wherein the sensor circuit further comprises a rectifier that rectifies an AC voltage from the secondary coil into a DC voltage.

17. The system of claim 15, wherein the sensor circuit further comprises a voltage divider and a zener diode.

18. The system of claim 9, wherein:
the charging coil, the sensor circuit, and the controller are parts of a charger; and
the system further comprises the implantable medical device that includes a receiving coil inductively coupled to the charging coil; and
the implantable medical device is configured to electrically short the receiving coil to ground repeatedly in response to a determination that the rechargeable battery no longer needs to be charged.

19. A system, comprising:
an implantable medical device that includes:
a rechargeable battery;
a receiving coil; and
a first controller, wherein the first controller is configured to electrically short the receiving coil to ground repeatedly in response to a determination that the rechargeable battery has been sufficiently charged; and
a charger that charges the implantable medical device, wherein the charger includes:
a charging coil that is inductively coupled to the receiving coil;
a sensor circuit coupled to the charging coil, wherein the sensor circuit is configured to detect an electrical current flowing through the charging coil or a voltage across the charging coil; and
a second controller coupled to the sensor circuit and to the charging coil, wherein the second controller is configured to:
compare an output of the sensor circuit with a predefined pattern; and
based on a match between the output of the sensor circuit and the predefined pattern, communicate a feedback signal to a user of the charger or terminate charging of the implantable medical device.

20. The system of claim 19, wherein the sensor circuit comprises a transformer, the transformer including:
a primary coil that is coupled to the charging coil in series; and
a secondary coil that is electromagnetically coupled to the primary coil.

* * * * *